(12) United States Patent
Kadota et al.

(10) Patent No.: US 6,319,692 B1
(45) Date of Patent: Nov. 20, 2001

(54) METHODS FOR TRANSFERRING GENE INTO CHROMOSOME

(75) Inventors: Mariko Kadota; Mayumi Kiwaki; Saeko Sawaki; Yukio Shirasawa; Harue Sone; Tomoyuki Sako, all of Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/202,893

(22) PCT Filed: Jun. 25, 1997

(86) PCT No.: PCT/JP97/02187

§ 371 Date: Dec. 22, 1998

§ 102(e) Date: Dec. 22, 1998

(87) PCT Pub. No.: WO97/49820

PCT Pub. Date: Dec. 31, 1997

(30) Foreign Application Priority Data

Jun. 26, 1996 (JP) .................................................. 8-184266
Sep. 6, 1996 (JP) .................................................. 8-257764

(51) Int. Cl.[7] .................................................. C12P 19/34
(52) U.S. Cl. .................. 435/91.1; 536/23.1; 435/320; 435/6; 435/471; 435/91.4; 435/91.42; 435/235.1; 935/23; 935/24
(58) Field of Search .................. 536/23.1; 435/320.1, 435/6, 471, 91.4, 91.42, 235.1, 252.3; 935/23, 24

(56) References Cited

U.S. PATENT DOCUMENTS 5,393,665   2/1995   Fayerman et al. ................ 435/172.3

FOREIGN PATENT DOCUMENTS

| 354727 | 2/1990 | (EP) . |
|---|---|---|
| 55-113718 | 9/1980 | (JP) . |
| 2-86781 | 3/1990 | (JP) . |
| 2-128692 | 5/1990 | (JP) . |
| 3-259086 | 11/1991 | (JP) . |
| 4-5236 | 1/1992 | (JP) . |
| 4-58890 | 2/1992 | (JP) . |
| 5-25055 | 2/1993 | (JP) . |
| 6-116155 | 4/1994 | (JP) . |

OTHER PUBLICATIONS

Gabriel, K et al, "The actinophage RP3 DNA integrates site–specifically into the putative tRNA–arg–(AGG) gene of Streptomyces rimosus", Nucleic Acids Research, 1995, vol. 23, No. 1, pp. 58–63.*

Chirstiansen, B et al, "A resolvase–like protein is required for the site–specific integration of the temperate lactococcal bacteriophage TP901–1", Journal of bacteriology, Sep. 1996, vol. 178, No. 17, pp. 5164–5173.*

Uchiumi, T et al, "A chromosome integrative vector system utilizing DNA fragments of a lysogenic phage of Rhizobium leguminosarum", Journal of General Microbiology, 1993, vol. 139, pp. 2371–2377.*

Kadota et al., "Physical Mapping of the Virion and the Prophage DNAs of a Temperate *Lactobacillus* phage Ø FSW", (1984), pp. 423–430, *Journal of General Microbiology*, 130.

Diederich et al., "New Cloning Vectors for Integration into the λ Attachment Site attB of the *Escherichia coli* Chromosome", (1992), pp. 14–24, *Plasmid*, 28.

Dupont et al., "Characterization of Genetic Elements Required for Site–Specific Integration of *Lactobacillus delbrueckii* subsp. bulgaricus Bacteriophage mv4 and Construction of an Integration–Proficient Vector for *Lactobacillus plantarum*", (1995), pp. 586–595, *Journal of Bacteriology*, 177.

Horinouchi et al., "Nucleotide Sequence and Functional Map of pC194, a Plasmid That Specifies Inducible Chloramphenicol Resistance", (1982), pp. 815–825, *Journal of Bacteriology*, 150.

Sambrook et al., "Molecular Cloning", (1989), A Laboratory Manual 2nd Edition.

Kadota et al., "Prophage Origin of a Virulent Phage Appearing on Fermentations of *Lactobacillus casei* S–1", (1983), pp. 669–674, *Applied and Environmental Microbiology*, 45.

Kadota et al., "Shuttle Plasmid Vectors for *Lactobacillus casei* and *Escherichia coli* with a Minus Origin", (1991), pp. 3292–3300, *Applied and Environmental Microbiology*, 57.

Ye et al., "Nucleotide Sequence and Genetic Characterization of Staphylococcal Bacteriophage L54a int and xis genes", (1989) pp. 4146–4153, *Journal of Bacteriology*, 171.

* cited by examiner

*Primary Examiner*—John S. Brusca
*Assistant Examiner*—Jeffrey S. Lundgren
(74) *Attorney, Agent, or Firm*—Frishauf, Holtz, Goodman, Langer & Chick, P.C.

(57) ABSTRACT

Methods for transferring a foreign gene into a host chromosome by integrating the foreign gene into a vector by utilizing a lysogenic phage, for the purpose of deleting unnecessary genes derived from the vector, except for the foreign gene. One method comprises (a) preparing a vector with a lysogenic phage integration site (such as an attP site) arranged between a first partial sequence of the objective foreign gene to be transferred, but lacking one terminal region thereof and a second partial sequence of the gene, but lacking the other terminal region, the second partial sequence having an overlapping region with a portion of the first partial sequence; (b) integrating the vector obtained in step (a) into the host chromosome; and (c) screening from among the recombinants obtained in step (b) a recombinant from which unnecessary genes originating in the vector have been deleted owing to the homologous recombination mechanism functioning in the overlapping region between the first and second partial sequences.

19 Claims, 14 Drawing Sheets

1' (φFSW)
MASISSYKLKDGKKAWEFYIFAGVDPQTGKEIKIHRRGFPTEKIAQQEATLAEAEIIKGHSHYQTERILMADYLNQWIT-KLK
                                                          *    *...    *
1 (φL54a)                                         MFRLEEKIKEKLNNKSSSELKTLTFHALLDEWLEYHIK

VN-VKEGSMIIYRYNLKKYIIPKIGDIRLAKYTLKEHQEFISSLFNDGLSLNTVKLINGTLHNALKKAVAI-GY----ITKNP
 .*....     *.  .......    *    *.**..*...*   .*  *     *
TSGFKVTTLDNLKTRIKNIKKNSSQNLLLNKIDTKYMQTFINEL-SNVYSANQVKRQLGHMKEAIKYAVKFYNYPNEHILNSV

Domain 1
TV----GVEFSAYAKDNSKKLHFWTKD----QVGSFI---EAAEEDKEPMWLSFFVTLID-CGLRVGEAMALRWSDIDFSKNTLSV
*.    .*  **  ..    *.**..        *.       ..  ...  *.*..  ....*.   .
TLPKKSKTIEDIEKEEAKMYNYLEMEQVIQIRDFILNDNNMQYRARILVAGAVEVQALTGMRIGELLALQVKDVDLKNKTIAI NATRIYRAETGSNAGKIALDRPKTLSSKRTEYMTARVNDLLQQQYERHFSHGNVQGFRFSTSHNNDFVFTYSSDAKFGQPLRS
*.**.*..  .  *.   *  ..***   *.*.**  * *  **.       *                  .** .*
NGT-IHRIKCNAGFGH--KDTTKTAGSKRKIAINSRIANVL---KKIMLENKKMQQWE-PSYVDRGFIFT----TCQGNPMQG Domain 2
RATTGAFNRITNRAGL-PHIRIIHDLRHTHAVLMREAGLSLDDIKDDLGHKDISTT-QIYAEISPAKKKENHQQFEKYLNQX
.*****  *.  * .. .* *** .*.   .* .*.** *.* *.* .  .*..    *..*.* *.*.*
SRINKRLSSAAESLNINKKVTTHTLRHTHISLLAEMNISLKAIMKRVGHRDEKTTIKVYTHVTEKMDRELEQKLEKLVY

F I G. 4

|  | domain 1 |
|---|---|
| Int(λ) E. coli | RLAMELAVVTGQRVGDLCEMKWSDIVDG |
| Int(HK22) E. coli | RLAMDLAVVTGQRVGDLCRMKWSDINDN |
| Int(φ80) E. coli | VFLVKFIMLTGCRTAEIRLSERSWFRLD |
| Int(P4) E. coli | MIAVKLSLLTFVRSSELRFARWDEFDFD |
| Int(P22) Salmonella typhimurium | KSVVEFALSTGLRRSNIINLEWQQIDMQ |
| Int(186) E. coli | ETVVRICLATGARWSEAESLRKSQLAKY |
| Int(HP1) Haemophilus influenzae | GLIVRICLATGARWSEAETLTQSQVMPY |
| Int(L54a) Sta. aureus | AGAVEVQALTGMRIGELLALQVKDVDLK |
| Int(φLC3) Lc. lactis | PTMLFIISITGMRASEAFGLVWDDIDFN |
| Int(φadh) L. gasseri | YALFKMLYLTGMRLGEGCGLLVKNIFQN |
| ORF2(Tn1545) Str. preumoniae | YDEILILLKTGLRISEFGGLTLPDLDFE |
| Int(φFSW) | SFFVT<u>L</u>ID–CG<u>L</u>R<u>V</u>GEAMA<u>L</u>RWSDIDFS |
| consensus | ––LV–L–L–TGMR–SEL–––LR––DI––– |
|  | * |
| Int(mv4) L. delbrueckii subsp. bulgaricus | YVFFLLLATTGLRKRRSTSPGLVGHRLR |

FIG. 5a domain 2

| | |
|---|---|
| Int(λ) E.coli | HELRSLSA-RLYEKQ---ISDKFAQHLLGHKS-DTMASQYR- |
| Int(HK22) E.coli | HELRSLSA-RLYRNQ---IGDKFAQRLLGHKS-DSMAARYRD |
| Int(φ80) E.coli | HDMRRTIATNLSELG---CPPHVIEKLLGHQM-VGVMAHYN- |
| Int(P4) E.coli | HGFRTMARGALGESG-LWSDDAIERQSLHSERNNVRAAYIH |
| Int(P22) Salmonella typhimurium | HDLRHTWASWLVQAG---VPISVLQEMGGWES-IEMVRRYAH |
| Int(186) E.coli | HVLRHTFASHFMMNG---GNILVLQRVLGHTD-IKMTMRYAH |
| Int(HP1) Haemophilus influenzae | HVLRHTFASHFMMNG---GNILVLKEILGHST-IEMTMRYAH |
| Int(L54a) Sta. aureus | HTLRHTHISLLAEMN--ISLKAIMKRVGHRDEKTTIKVYTH |
| Int(φLC3) Lc. lactis | HGLRHTHASVLLYHG--VDIMTVSKRLGHASVAITQQTYIH |
| Int(φadh) L.gasseri | HIFRHTHVSKLAEEG--YPLSLITDRVGHANSDITRKIYLH |
| ORF2(Tn1545) Str. preumoniae | HSLRHTFCTNYANAG--MNPKALQYIMGHAN-IAMTLNYYA |
| Int(φFSW) | HDLRHTHAVLMREAG---LSLDDIKDDLGHKD-ISTTQIYAE |
| consensus | H-LRHT-AT-L---G----I--IQ-LLGH----I--T--Y-H |
| | *          *                    * |
| Int(mv4) L.delbrueckii subsp.bulgaricus | HGFRHTFASLLITADPSIKPTDVQAILGHESIDITMEIYMH |

FIG. 5b

1' (ORF8)
SSQPETPSAPVTPVPSQPAKSNAASDSDYAQTGVFKPSTTVNIRTGAGTGYTAVGSYVPGESLVYDHVYIRGSYVVARYLSYSGRYHYV

90' (ORF8)
ALGVNGGESYGSRSSGYTSLVSHTYYTVRSGDSFWSIASKYGISMYTLAANNGKSIYSLIYPGESLYIK
.  .  .  .*..  .***.  * .. .**.*. .* .  .* *.. **.*.*.*
GGNTGGGTVNPGTGGSNNQSGTNTYYTVKSGDTLNKIAAQYGVSVANLRSWNGISG-DLIFVGQKLIVKKGASGNTGGSGNGG......
338' (autolysin)

FIG. 6

```
                BssHII
attP    TTCAAATCGCGCAAGCCCTTGCCATTAAAGGGCGGCGTTCAATTCCTTGGTCATATCCTCA-
attR    TTTCAAATCGCGCAAGCCCTTGCCATTAAAGGGCGGCGTTCAATTCCTTGGTCATATCCTCA-
attL    TCCAAACGACCTCAAACCCACGCTATTAAGGCCGTGCGTTCAATTCCTTGGTCATATCCTCG-
attB    TCCAAACGACCTCAAACCCACGCTATTAAGGCCGTGCGTTCAATTCCTTGGTCATATCCTCG- Eco52I      XmnI
(attP)  TAACCCGGGACGGCCGAGCAATGCGAACATGTTCTTCTTGTTGATTTGCTTGAACACTGATTT
(attR)  TAACCCGGGACGGCCGAGCAATGCGAACATGTTCTTCTTGTTGATTTGCTTGAACACTGGTTGA
(attL)  TAACCCGGGACGGCCGAGCAATGCGAACATGTTCTTCTTGTTGATTTGCTTGAACACTGATTT
(attB)  TAACCCGGGACGGCCGAGCAATGCGAACATGTTCTTCTTGTTGATTTGCTTGAACACTGGTTGA
```

FIG. 7

```
(ORFattB)
         AADKELREGTGAGKDFRGFIDLPVNYDKDEFARIKAAAKKVQGNSQVFVAIGIGGSYLGARM
         *...*.*:***.*:**.*:..********.*****.**.**.*.****:********:***
MTHIRFDYSKALSFFGEHELTYLRDAVKVAHHSLHEKTGVGNDFLGWLDLPVNYDKEEFARIQKAAAKIQADSDVLLVIGIGGSYLGARA
(G6P isomerase A)

AVDFLSQTF-RNLDPDLK-FPEVYFAGNSISGTYLADLLDIIGDRDFSINVISKSGTTTEPSIAFRVLKAKLIEKYGKDGAKERIYATTD
*..*.*...*....*..*.******.*..*.**.**..*.........****************..*...*.*.********
AIEMLHHSFYNALPKEKRNTPQIIFVGNNISSTYMKEVMDLLEGKDFSINVISKSGTTTEPAIAFRIFRKLLEEKYGKEEARKRIYATTD

RAKGALKQEADAEGYEEFVVPDDVGGRFSVMSAVGLLPIAVAGGDIDEMMRGLGDGRKAYASADLKENEAYQYAALRNILYRKGYTTELL
**.****.*.******.*.********.**..*.*.*.*********.*.*.*..*.****.***.*.*.*.**.***.******.***
RARGALKTLATAEGYETFIIPDDVGGRYSVLTAVGLLPIAVSGANIEEMMKGAAQAREDFSSSELEENAAYQYAAIRNILYNKGKTIELL

ENYEPTLQYLGEWWKQLMGESEGKDQKGIYPSSANFSTDLHSLGQYIQEGLRNLMETVVWVEEPNRDLTIPEDANNLDGLGYLAGKKMSF
****.***.******.******.*.*********************.*.***..**.*.*:..*****.........*****..*
INYEPALQYFAEWWKQLFGESEGKDQKGIFPASANFSTDLHSLGQYIQEGRRDLFETVLKVEKPRHDLVIEAEENDLDGLNYLAGKTVDF

VNRKAYEGVVLAHTDGGVPVMTVSIPKQDAYTLGYLIYFFEAVVSISGYLNGINPFNQPGVEAYKKNMFALLGRPGYEDMTKELNARP
**.**..*********.......***********.***.****:..*.*********.*********:**..*.*****
VNTKAFEGTLLAHTDGGVPNLVITLPELNEYTFGYLVYFFEKACAMSGYLLGVNPFDQPGVEAYKVNMFALLGKPGYEEKKAELEKRLK
```

F I G. 9a (ORFattB)
AADKELREGTGAGKDFRGFIDLPVNYDKDEFARIKAAAKKVQGNSQVFVAIGIGGSYLGARMA
**.*.*.*.**.*..*.*...*.....*..*.**************.*.*************
MAISFDYSNALPFMQENELDYLSEFVKAAHHMLHERKGPGSDFLGWVDWPIRYDKNEFSRIKQAAERIRNHSDALVIGIGGSYLGARAA
(G6P isomerase B)

VDFLSQTFRNLDPDLKFPEVYFAGNSISGTYLADLLDIIGDRDFSINVISKSGTTTEPSIAFRVLKAKLIEKYGKDGAKERIYATTDRAK
..* *....**..**....*.*****************.***.....*..*.**.*
IEALSHTFHNQMNDTT--QIYFAGQNISSTYISHLLDVLEGKDLSINVISKSGTTTEPAIAFRIFRDYMEKKYGKEEARKRIYVTTDRTK

GALKQEADAEGYEEFVVPDDVGGRFSVMSAVGLLPIAVAGGDIDEMMRGLGDGRKAYASADLKENEAYQYAALRNILYRKGYTTELLENY
**..*****.**..******************..**.*.***.*****..*.**
GALKKLADQEGYETFVIPDNIGGRYSVLTAVGLLPIAVAGLNIDRMMEGAASAYHKYNNPDLLTNESYQYAAVRNILYRKGKAIELLVNY

EPTLQYLGEWWKQLMGESEGKDQKGIYPSSANFSTDLHSLGQYIQEGLRNLMETVVWVEEPNRDLTIPEDANNLDGLGYLAGKKMSFVNR
**.*.*.******.*****.*.*.*****..*.*.*.***************...**
EPSLHYVSEWWKQLFGESEGKDQKGLFPASVDFTTDLHSMGQYVQEGRRNLIETVLHVKKPQIELTIQEDPENIDGLNFLAGKTLDEVNK

KAYEGVVLAHTDGGVPVMTVSIPKQDAYTLGYLIYFFEAVVSISGYLNGINPFNQPGVEAYKKNMFALLGRPGYEDMTKELNARP
**..*.*.***..*..*.****.*.****************.*.*.*
KAFQGTLLAHVDGGVPNLIVELDEMNEYTFGEMVYFFEKACGISGHLLGVNPFDQPGVEAYKKNMFALLGKPGFEDEKAALMKRLSK

FIG. 9b

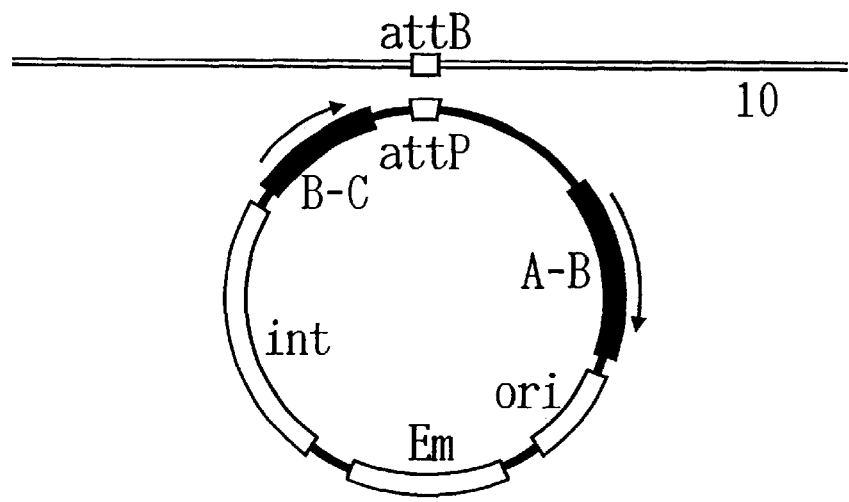
F I G. 10a
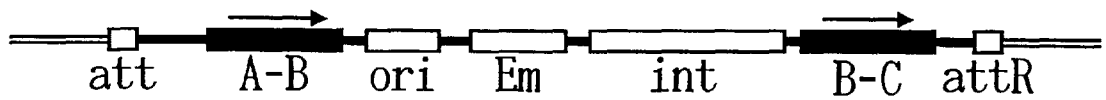
F I G. 10b
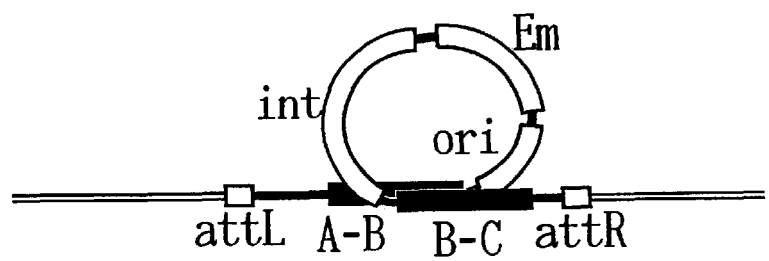
F I G. 10c
F I G. 10d

METHODS FOR TRANSFERRING GENE INTO CHROMOSOME

TECHNICAL FIELD

The present invention relates to a method for transferring a foreign gene into a host chromosome, and more specifically, to a method for transferring a foreign gene into a chromosome by using a lysogenic vector, wherein genes originating in the vector and being necessary at the time of transfer but unnecessary for the expression and conservation of the foreign gene are finally deleted. Additionally, the present invention relates to a vector capable of integrating a foreign gene into the chromosome of for example *Lactobacillus casei* (referred to as *L. casei* hereinafter).

BACKGROUND ART

By using plasmids, foreign genes have been transferred into host cells of various microorganisms including *Escherichia coli* (referred to as *E. coli* hereinafter). So as to allow the characteristic properties of a foreign gene to be exerted in host cells in a more stable manner, attempts have been made to integrate a foreign gene into a host chromosome by using a lysogenic phage.

Meanwhile, *L. casei* Shirota strains, YIT9018 and YIT9029, have been utilized widely in for example lactic acid beverages and fermented milk, and it is revealed that these strains have excellent physiological actions, particularly antitumor activity, blood cholesterol reducing action, hypotensive action and anti-ulcer effect (Japanese Patent Laid-open Nos. 113718/1980, 5236/1992, 25055/1993, and 116155/1994).

A number of reports have been issued about shuttle vectors in hosts such as these lactic acid bacteria, particularly *L. casei* (see Japanese Patent Laid-open Nos. 128692/1990, 259086/1991, and 58890/1992). Most of these shuttle vectors in reports have been prepared via transformation as plasmids, so not any of these shuttle vectors has been satisfactory in terms of stability.

According to a conventional method for transferring a foreign gene into a host cell by utilizing a lysogenic phage, not only the objective foreign gene but also DNA sequences unnecessary after the transfer are simultaneously transferred. For example, a site-specific recombination enzyme gene region, a chemically resistant gene region necessary for recombinant selection, and a replication origin functioning in *E. coli* are simultaneously integrated into the chromosome of a host, but functionally, these regions are not necessary after the transfer of the gene.

From the standpoint of the subsequent utilization of a transformant, these regions functionally unnecessary after the transfer of the gene may sometimes be disadvantageous.

SUMMARY OF THE INVENTION

It is an object of the present invention to provide a method for transferring a foreign gene into a chromosome, wherein unnecessary genes originating in a vector, etc., except for the foreign gene, can be deleted finally. It is the other object of the present invention to provide a recombination-type vector preferable for integration into the chromosome of *L. casei* strain YIT9029, in particular.

According to the present invention, more specifically, unnecessary genes derived from a vector, etc., except for the foreign gene, can be deleted finally by contriving procedures to integrate the foreign gene in the vector by utilizing a lysogenic phage just when the foreign gene is to be transferred into a host cell.

In one embodiment of the present invention, a method for integrating a foreign gene into a host chromosome by using a vector with the properties of lysogenic phage, comprises:
a first step of modifying the vector so that a lysogenic phage integration site (attP site) might be arranged between a first partial sequence being composed of the foreign gene to be transferred but lacking one terminal region thereof and a second partial sequence being composed of the gene but lacking the other terminal region thereof and having an overlapping region with a portion of the first partial sequence;
a second step of integrating the vector obtained in the first step into the host chromosome; and
a third step of screening from among the recombinants obtained in the second step a recombinant from which unnecessary genes originating in the vector have been deleted owing to the homologous recombination mechanism functioning in the overlapping region between the first and second partial sequences.

In accordance with the present invention, the term "vector with the characteristic properties of lysogenic phage" means a vector to be functionally integrated into a host chromosome when transferred in a host cell. More specifically, any vector having an integration site (for example, attP site) triggering the recombination of a different recombination site (for example, attB site) into the chromosome of a host cell may be satisfactory. A recombinant prepared by integrating a foreign gene into a host chromosome by using such vector carries integrated genes derived from the vector, together with the foreign gene. In accordance with the present invention, therefore, it should be prepared, prior to integration, a vector with a lysogenic phage integration site (attP site) arranged between a first partial sequence lacking one terminal region of the objective foreign gene for transfer and a second partial sequence lacking the other terminal region thereof and having an overlapping region with a portion of the first partial sequence. At the integration step, the vector is integrated into the chromosome of a host for promoting homologous recombination to recover a recombinant.

These first partial sequence and second partial sequence have an overlapping region to each other. As the length of the sequence in the overlapping region is shorter, the frequency of the homologous recombination after integration is decreased, so it is difficult to delete the unnecessary genes via such homologous recombination. Even by alternatively elongating the length of the sequence of the overlapping region, for example by allowing the first partial sequence and the second partial sequence to have absolutely the same sequence, with no deletion of any terminal region of the foreign gene, such homologous recombination occurs. When intending to use the expression of the foreign gene as a marker for final selection, potentially, there will be no chance that a transformation recombinant with the deletion of unnecessary vector-derived genes is selected among the resulting recombinants. Therefore, the lower limit of the length of the sequence of the overlapping region is satisfactorily a length at which the homologous recombination mechanism functions at a sufficient frequency. The length of the sequence of the overlapping region has not upper limit from the standpoint of homologous recombination, but when intending to use the expression of the foreign gene as a marker, the length may satisfactorily be a length at which no foreign gene expression occurs in the partial sequences with the deletion of one terminal region.

The first partial sequence and the second partial sequence are arranged in a direction along which the homologous recombination occurs in the overlapping region, so that the resulting sequence from such homologous recombination serves as the essential foreign gene. More specifically, the first and second partial sequences should be arranged toward the same direction, to align the individual termini N and C of the foreign gene so as to interpose the integration site (attP site) of the lysogenic phage between the termini.

In accordance with the present invention, the term "foreign genes" does not necessarily mean those derived from bacteria other than a host bacterium into which the gene is to be integrated, but means those from the same species of bacteria and those from the same bacterial strain, for example a gene harbored on a plasmid to be transferred into the chromosome. Furthermore, the foreign gene may satisfactorily be a set of genes as a combination of plural types of protein information (for example, the gene of an enzyme composed of plural subunits, in its entirety).

So as to select a recombinant where transformation has occurred after the deletion of the unnecessary genes derived from a vector, the loss of a chemical resistance derived from the vector may be used as a marker. As has been described above, however, the most simple process comprises preliminarily confirming the expression of an integration-intended foreign gene and then using the expression as a marker. More specifically, the deletion of the unnecessary genes derived from the vector means that the foreign gene is arranged at the intact state thereof after homologous recombination. By using the expression of the foreign gene as a marker, therefore, the aforementioned selection may be carried out.

By using a L. casei vector carrying the gene region of the site-specific recombination enzyme (integrase; Int) and the integration site into a host chromosome (attP region), both the region and the site being derived from the lysogenic phage φFSW of L. casei stain YIT9018, a chemically resistant gene region functioning in lactic acid bacteria and Escherichia coli, a replication origin functioning in Escherichia coil (referred to as E. coil hereinafter), and a cloning site, in another embodiment of the present invention, a method for integrating a foreign gene (A-B-C) composed of regions A, B and C (wherein the regions A and C represent partial sequences including one terminus of the foreign gene; and the region B represents an arbitrary intermediate sequence between the partial sequences) is provided, the method comprising:

- a first step of modifying the vector so that the attP site might be arranged between a first partial sequence (A-B) lacking one terminal region (C) of the foreign gene (A-B-C) to be transferred and a second partial sequence (B-C) lacking the other terminal region (A) of the gene;
- a second step of integrating the vector obtained in the first step into the chromosome of L. casei to recover a recombinant; and
- a third step of screening from among the recombinants obtained in the second step a transformation recombinant with no unnecessary genes including the site-specific recombinant enzyme region, the chemical resistance region and the replication origin because of the deletion thereof owing to the homologous recombination mechanism.

In accordance with the present invention, the method for chromosomally transferring the foreign gene can be applied to any bacterium by using a combination of a vector and a host bacterium, where the characteristic properties of a lysogenic phage can be utilized. Hence, the present invention is preferable for transferring the foreign gene of L. casei by using a L. casei vector (vector pMSK74, in particular), but it is needless to say that the present invention is not limited to the L. casei vector. Other vectors may also be usable, specifically including vectors in combination with φLC3 phage of Lactococcus lactis, the φadh phage of Lactobacillus gasseri, the mv4 phage of Lactobacillus delbrueckii•subsp.•bulgaris, Escherichia coli in combination with λ phage, HK22 phage, φ80 phage, P4 phage, and 186 phage and the like (Reference A: L. Dupont et. al., J. Bacteriol.177: 586–595 (1995)).

As has been described above, in accordance with the present invention, an objective foreign gene to be transferred into a vector is not integrated thereinto as it is; but the objective foreign gene is preliminarily fragmented into two partial sequences with an overlap in an arbitrary intermediate sequence of the foreign gene, and the resulting two partial sequences are then integrated into the two sides of the attP sequence of the vector for the purpose of deleting unnecessary genes derived from the vector, etc., capable of utilizing the characteristic properties of a lysogenic phage, except for the foreign gene, and therefore, the unnecessary genes derived from the vector and the like, except for the foreign gene, are also integrated at a considerable probability in the resulting recombinants, which should then be selected out.

Provided that the objective foreign gene to be transferred is represented by the general formula A-B-C (wherein A and C independently represent sequences including one terminal sequence; and B represents an arbitrary intermediate sequence between A and C), a first partial sequence A-B as a partial sequence of A-B-C and a second partial sequence B-C thereof (A-B and B-C individually contain an overlapping sequence in the sequence B) are arranged on the two sides of the attP region of the vector and then integrated into the chromosome of a host, whereby a portion interposed between A-B and B-C is deleted at a considerable probability owing to a certain spontaneous homologous recombination mechanism, so that the sequence A-B-C is transferred into the chromosome.

So as to transfer the foreign gene into the chromosome of L. casei in accordance with the present invention, preferably, use is made of for example a L. casei vector carrying the int region and attP region derived from the lysogenic phage φFSW of L. casei strain YIT9018, a chemically resistant gene region functioning in lactic acid bacteria and Escherichia coli, a replication origin functioning in E. coli and an appropriate cloning site.

Specifically, the vector carries the gene region of the site-specific recombination enzyme (integrase; Int) and the integration site into a host chromosome (attP region), the region and the site both being derived from the lysogenic phage φFSW of L. casei strain YIT9018, a chemically resistant gene region functioning in lactic acid bacteria and E. coli, a replication origin functioning in E. coli, and a cloning site.

More specifically, the vector carries the gene region of the site-specific recombination enzyme (integrase; Int) and the integration site into a host chromosome (attP region), the region and the site being derived from the lysogenic phage φFSW of L. casei strain YIT9018, an Enterococcus faecalis-derived erythromycin (Em) resistant gene functioning in lactic acid bacteria and E. coli, and a replication origin derived from E. coli.

With no specific limitation, a chloramphenicol (Cm) resistant gene was used in the following example as a foreign gene to be transferred. The manner to integrate two partial sequences prepared by fragmenting the foreign gene on the two sides of the attP region of the vector may appropriately be designed, by utilizing the restriction sites of the vector or by identifying the restriction sites and the like carried in the gene to be transferred. So as to subsequently induce a homologous recombination mechanism, the sequence B (overlapping part) in the general formula is required to be of a sufficient length (preferably, a length of about 200 to 1,000 nucleotides, and more preferably, a length of about 400 to 600 nucleotides).

In the following example, procedures are effected for once transferring the Cm resistant gene corresponding to A-B-C on the two sides of the attP region and subsequently deleting excess parts to consequently allow the partial sequences A-B and B-C to be transferred as intended, but it is needless to say that it is not limited to the manner alone.

A gene transfer vector prepared by transferring the partial sequences A-B and B-C in a vector pMSK742 is integrated into the chromosome of L. casei, involving transformation. Using as a marker the Em resistant gene of pMSK742, the resulting recombinants are subjected to screening, to recover a recombinant having been integrated into the chromosome as intended. The thus prepared vector still carries the pMSK742-derived Int region and Em resistant gene region, where the Cm gene as intended to be transferred still remains as it is separated in two regions and is not integrated at the full-length state.

When the resulting transformant is subcultured by using as a marker the Em resistance and the Cm resistance, strains with Cm resistance and Em sensitivity (having lost the Em resistance) can be recovered at a considerable probability ($10^{-3}$). This is due to the occurrence of homologous recombination between the integrated A-B region and the B-C region, so that the portion interposed between the A-B region and the B-C region is deleted. The probability is sufficiently higher than the probability of the loss of Em resistance by general Em resistant strains through mutation. Hence, the integration of the foreign gene A-B-C and the excision of the unnecessary regions derived from the vector can be facilitated due to the designed mechanism.

The vector for L. casei in accordance with the present invention particularly carries those described below;

the Int region and attP region derived from the lysogenic phage φFSW of the L. casei strain YIT9018;

a chemically resistant region functioning in lactic acid bacteria and E. coli;

a replication origin derived from E. coli; and an appropriate cloning site.

The Int region in the L. casei vector in accordance with the present invention means a region coding for the site-specific recombinant enzyme (so-called integrase). Integrase, also referred to as Int protein or phage DNA insertion enzyme or the like, is one of proteins generated in a host bacterium infected with a phage and is an essential enzyme for allowing a phage genome to be integrated into the bacterial chromosome after the occurrence of mutual site-specific recombination between a specific site of the phage DNA, namely attP and a specific site in the chromosome of the host bacterium, namely attB. Together with the products of the xis (excisionase) gene, the enzyme further functions to excise the phage. As such Int region, the Int region from the lysogenic phage φFSW of L. casei is selected in one embodiment of the present invention.

Alternatively, the attP region means the integration site into the chromosome of a host bacterium. Temperate phage (lysogenic phage) is integrated at the fixed site (attP) in the chromosome of a host bacterium. When a cyclic phage is integrated in the chromosome of a host bacterium, for example, the annular phage and the chromosomal DNA are subjected to recombination via the individual attachment sites, to form a structure of so-called "character 8" and then form a unit. The attP region corresponds to the integration site of the phage.

The chemically resistant region serves as a marker in detecting a transformation recombinant. Therefore, the vector may satisfactorily carry a chemically resistant region functioning uniquely in a lactic acid bacterium and a different chemically resistant region functioning singly in E. coli; otherwise, the vector may satisfactorily carry one chemically resistant region functioning both in lactic acid bacteria and in E. coli.

A region derived from E. coli may be selected as the replication origin. In this case, procedures for transferring a foreign gene into the vector should be carried out by using E. coli and a vector system thereof (so-called EK system), whereby the replication origin securely promotes the replication inside the host bacterium E. coli.

The term "cloning site" means the recognition and cleavage site of a restriction endonuclease for the insertion of the foreign gene. Herein, such a site should be selected that might not divide for example the int region, the attP region, the chemically resistant region or the replication origin through the insertion of the foreign gene.

The vector pMSK742 for L. casei, which is preferably used in the method of the present invention, has been deposited as FERM BP-5978 on Jun. 20, 1996, at the Life Engineering and Industrial Technology Research Institute, the Agency of Industrial Science and Technology, at 1-3, Higashi 1-chome, Tsukuba-shi, Ibaraki, Japan. The pMSK742 is of a size of 4,031 bp, containing the Int region and attP region derived from the lysogenic phage φFSW of L. casei strain YIT9018. As a chemically resistant region, the vector carries the erythromycin (Em) resistant gene derived from Enterococcus faecalis. The Em resistant gene functions both in E. coli and lactic acid bacteria. The vector additionally contains the recognition and cleavage sites with restriction endonucleases XbaI, BspHI, KpnI, and HpaI and the like as the cloning sites.

BRIEF DESCRIPTION OF THE DRAWINGS

FIG. 4 is an explanatory view of the comparison in amino acid sequence between the integrase protein of φFSW and the integrase protein of phage L54a;

FIGS. 5a and 5b are explanatory views of the comparison in amino acid sequence between the two highly conserved regions (domain 1 and domain 2) found in the integrases of various phages and transposon;

FIG. 6 is an explanatory view of the homology between the protein encoded by ORF8 and the autolysin (N-acetylmuramoyl-L-alanine amidase) derived from Enterococcus faecalis;

FIG. 7 is an explanatory view of the comparison between the homologous region found in attP, attR, attL and attB and the DNA sequences around the region;

FIGS. 9a and 9b are explanatory views of the comparison between the translation product of the ORF (ORFattB) in SEQ ID No.3 and the proteins of glucose-6-phosphatase isomerases A and B derived from *Bacillus stearothermophilus*;

FIGS. 10a to 10d are explanatory views schematically depicting the processes of the method for transferring the foreign gene into the chromosome in one example in accordance with the present invention;

BEST MODE FOR CARRYING OUT THE INVENTION

Figure 1:
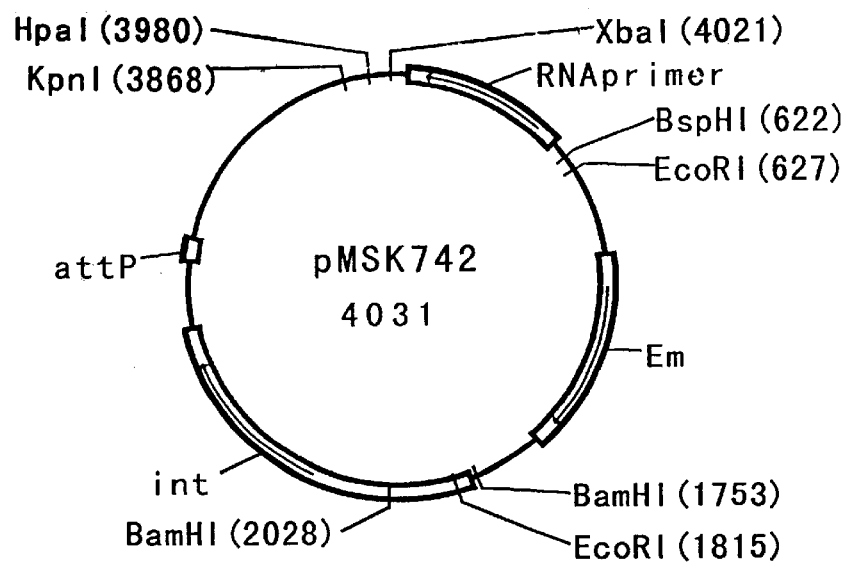
FIG. 1 depicts a restriction map of plasmid pMSK742.

The present invention will now be described in more detail in the examples.

1. Materials and Methods 1-1. Bacterial Strains and Culture Media for Use

*L. casei* YIT9029 (FERM BP-1366, non-φFSW-lysogenic bacterial strain) and YIT9018 (φFSW-lysogenic bacterial strain) were grown in MRS culture medium (Difco, USA) or ILS culture medium under aerobic conditions at 37° C. (stationary culture for liquid culture media).

*E. coli* JM109 was used as a host for preparing a recombinant plasmid. Because the expression of Cm resistance by the Cm resistant gene in plasmid pC194 of *Staphylococcus aureus* (Reference B: S. Horinouchi & B. Weisblum. Nucleotide sequence and functional map of pC194, a plasmid that specifies inducible chloramphenicol resistance, J. Bacteriol. 150: 815–825, 1982) is inducible, Cm at 0.5 μg/mL (concentration for the same growth level for Cm sensitive strains and Cm resistant strains) was essentially added thereto, irrespective of the use of resistant or sensitive bacterial strains, to allow a bacterial strain with the Cm resistant gene to express the resistance. If necessary, 20 μg/mL Em (concentration at which Em sensitive strains cannot grow) or 2.5 μg/mL Cm (concentration at which Cm sensitive strains cannot grow) was added to the medium. LB culture medium was used for the growth of *E. coil* JM109, to which 500 μg/mL Em was added, if necessary.

1-2. DNA Preparation and Procedures

DNA procedures were fundamentally based on the known cloning method (Reference C: J. Sambrook, E. F. Fritsch & T. Maniatis. Molecular Cloning A Laboratory Manual, Cold Spring Harbor Laboratory Press, 1989). The extraction procedures for chromosomal DNA from the *L. casei* strain YIT9029 were according to the known method (Reference D: M. Shimizu-Kadota, T. Sakurai & N. Tsuchida, Prophage origin of a virulent phage appearing on fermentations of *Lactobacillus casei* S-1. Appl. Environ. Microbiol. 45: 669–674, 1983). According to the method in the reference by Shimizu et al., φFSW phage DNA was prepared from a phage particle. For plasmid DNA extraction from *E. coli*, a kit manufactured by Promega Corporation, "Wizard (TM) Minipreps DNA Purification System", was used. DNA manipulation such as cloning was carried out with reference to the Sambrook's Reference C.

1-3. Transformation Method

By electroporation (Reference E: M. Shimizu- Kadota, H. Shibahara-Sone & H. Ishiwa, Shuttle plasmid vectors for *L. casei* and *E. coli* with a minus origin. Appl. Environ. Microbiol. 57: 3292–3300, 1991), the *L. casei* strain YIT9029 was transformed. When the DNA of pHS4611 replicable in YIT9029 is transferred into YIT9029 according to the method, a transformation recombinant can essentially be recovered at a frequency of $10^5$/μg DNA or more. *E. coli* transformation was promoted by using the JM109 competent cell manufactured by Toyobo Co., Ltd., according to the protocol of the said Company.

1-4. DNA Sequencing and Analysis

The DNA in the form of a plasmid was subjected to sequencing as it was. For the determination of the nucleotide sequence of a PCR product, the PCR product was directly used or the product was preliminarily purified on an agarose gel by using the SpinBind (TM) DNA Recovery System manufactured by TaKaRa Shuzo Co., Ltd. Appropriate 17-mer primers or larger ones were synthetically produced. The reaction was promoted by 373S DNA Sequencer by using "ABI PRISM (TM) Terminator Cycle Sequencing Ready Reaction Kit (Perkin Elmer Co.)". The nucleotide sequence was analyzed by using "GENETYX ver. 9.0" and "GENETYX-CD Bio DATABASE Software ver. 29.0", both manufactured by Software Development Company and a database "Entrez Release 21.0" manufactured by National Center for Biotechnology Information Co.

The chromosome structure in the YIT-9029-transformed recombinant was examined by PCR. The PCR product was purified on "Micro Spin (TM) S-400 HR Column" manufactured by Pharmacia Co.

1-5. PCR

By using the KOD polymerase manufactured by Toyobo Co., Ltd., and the buffer system #1 manufactured by Toyobo Co., Ltd., a cycle of 98° C. for 15 seconds, 60° C. for 5 seconds and 74° C. for 30 seconds was repeated 30 times for the PCR by using a DNA engine PTC-200 manufactured by MJ Research Co. Primers of 20-mer or more were appropriately synthesized as the primers for use.

Primer combinations, INT25 and INT27, INT20 and INT27, and INT21 and INT25, were used to detect attB, attL and attR, respectively, in the strain YIT9029 and the transformation recombinant. The nucleotide sequences of the primers INT20, 21, 25 and 27 are shown as parts of the nucleotide sequence of SEQ ID No.1 or 3 in the following sequence Listing. INT21 is the primer of the 20 nucleotides at positions 2501 to 2520 in SEQ ID No.1; and INT20 is the primer of the complementary chain of the 20-nucleotide sequence at positions 3144 through 3163 in SEQ ID No.1. Furthermore, INT25 is the primer of the 20 nucleotides at positions 884 to 903 in SEQ ID No.3; and INT27 is the primer of the complementary chain of the 20-nucleotide sequence at positions 1463 to 1482 in SEQ ID No.3.

A test bacterium was cultured overnight, and the resulting culture was rinsed in 1M Bis-Tris, pH 7.2 and suspended in an equal volume of distilled water. To the resulting suspension in a total volume of 18 μL were added 1 μL of N-acetyl-muramidase SG (500 μg/mL) manufactured by Seikagaku Kogyo Co., Ltd., and 8.5 μL of distilled water, for 1-hr reaction, and the resulting mixture was then subjected to PCR (in the total volume of 50 μL) by using the KOD polymerase kit manufactured by Toyobo Co., Ltd. By using "LA PCR in vitro Cloning Kit" manufactured by Takara Shuzo Co., Ltd., Tail-PCR capable of amplifying the structure of the boundary region between a known DNA sequence region and an unknown DNA sequence region was carried out.

1-6. Stability Test

A derivative of the test bacterial strain YIT9029 was cultured overnight in ILS with addition of 2.5 μg/mL Cm, and the resulting culture was diluted with ILS with addition of 0.5 μg/mL Cm by $10^{-5}$ fold and was then subjected to stationary culture at 37° C. Subsequently, the culture was subcultured, by similarly diluting every 24 hours the culture by $10^{-3}$ fold with ILS with addition of 0.5 μg/mL. By using an ILS plate with addition of 2.5 μg/mL Cm (selective plate) and an ISL plate with addition of 0.5 μg/mL Cm (non-selective plate), viable bacteria were counted in number. The generation number was calculated in log2(each viable cell count x dilution ratio/initial viable cell count).

2. Preparation of Recombinant Plasmid

It has been known that the recombination site on the phage genome of the lysogenic phage φFSW of *L. casei* strain YIT9018 is limited to the 1.3-kb XhoI DNA fragment (Reference F: M. Shimizu-Kadota & N. Tsuchida . J Gen. Microbiol. 130: 423–431, 1984). So as to enhance the stability in accordance with the present invention, a plasmid vector of recombination type into a prophage chromosome was designed and developed.

In the present Example, at first, the nucleotide sequence of the DNA in an about 3.8-kb region including the 1.3-kb XhoI DNA fragment of the phage genome was determined, to subsequently screen the open reading frame (ORF).

2-1. DNA Nucleotide Sequence in the Region Involved in the Site-specific Recombination on the φFSW Genome It has been well known on the basis of Southern hybridization that the phage genome of φFSW when lysogenized is recombined into the chromosome of the non-φFSW-lysogenic bacterium through Campbell-type site-specific recombination to be prepared as a prophage.

Figure 2:
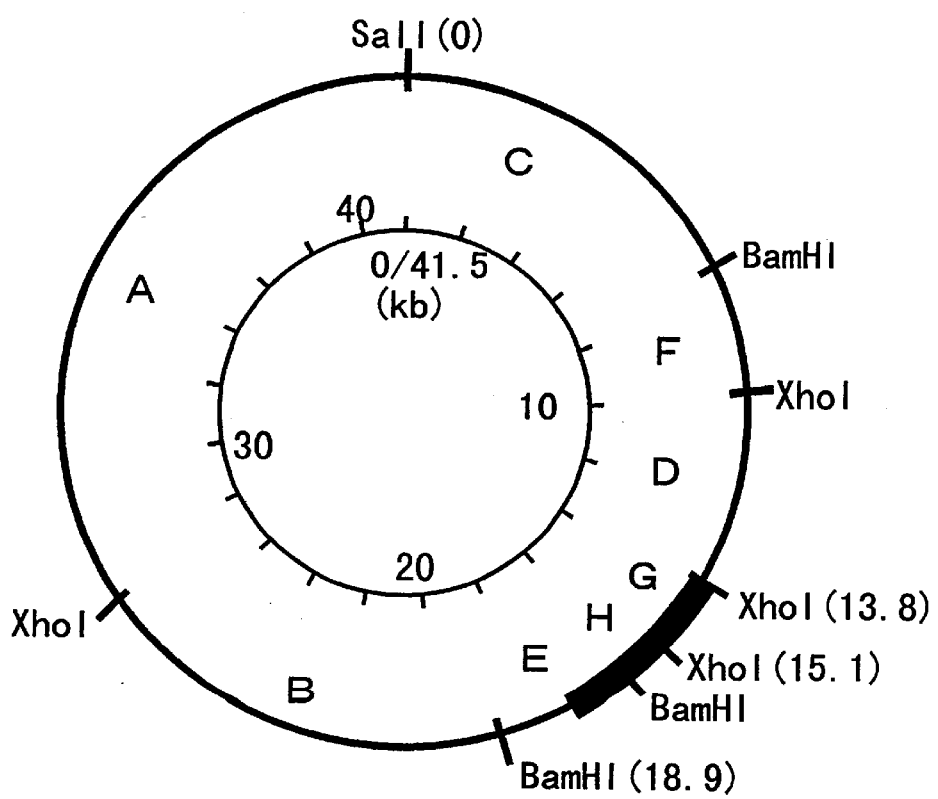
FIG. 2 depicts a restriction map of temperate phage φFSW.

FIG. 2 depicts a restriction map of the genome of the temperate phage φFSW of *L. casei* YIT9029. Using the single SalI cleavage site as a start point, the positions on the map are expressed in kb toward the clockwise direction. The positions for the site-specific recombination on the phage genome are limited to in between two XhoI cleavage sites present at 13.8 kb and 15.1 kb. The nucleotide sequence of the DNA in the region was determined, and on the basis of the screening of the open reading frame (ORF) and the translation product and the screening of similar regions in the amino acid sequences of known proteins (data not shown), a region possibly involved in the recombination of the prophage chromosome was supposedly present at a position with a higher numerical number (in kb) on the restriction map.

Over an about 2.5-kb region around the XhoI fragment, the DNA was sequenced. The region with the thus determined DNA sequence is shown in broad line in FIG. 2. The results are shown in SEQ ID No.1 in the following Sequence Listing, while SEQ ID No.2 indicates a partial amino acid sequence of SEQ ID No.1.

SEQ ID No.1 includes the int and attP regions of φFSW, the DNA sequence therearound and a putative int gene product. As the initiation codon of the int gene, possibly, three positions of methionine (Met) were confirmed. A first Met position was at nucleotide numbers 1509–1511 (positions); a second Met position was at nucleotide numbers 1716–1718 (positions); and a third Met position was at nucleotide numbers 1776–1778 (positions). Immediately upstream these positions were confirmed ribosomal RNA-binding polypurine sites (RBSS) (at nucleotide numbers (positions) 1493–1499, 1704–1708, and 1764–1770).

The Int gene termination codon is "TGA" at nucleotide numbers (positions) 2691–2693. Additionally, inverse repetitious nucleotide sequences (stem loops) were confirmed downstream the Int gene (nucleotide numbers 2753–2764 and 2770–2784 for 2700–2714 and 2716–2729, respectively). In the nucleotide sequence of SEQ ID No.1, herein, the names of main restriction endonucleases and the recognition and cleavage sites thereof are as follows; PvuI (nucleotide numbers (positions) 1–6); BssHII (nucleotide numbers (positions) 493–498, 2826–2831); EcoRV (nucleotide numbers (positions) 1503–1508); BamHI (nucleotide numbers (positions) 1770–1775); XhoI (nucleotide numbers (positions) 2311–2316, 2455–2460, 3844–3849); Eco52I (nucleotide numbers (positions) 2866–2871); XmnI (nucleotide numbers (positions) 2880–2889); and FspI (nucleotide numbers (positions) 3757–3762). As described below, furthermore, the attP core sequence is present at nucleotide numbers (positions) 2857–2896.

The 20-nucleotide primer at nucleotide numbers (positions) 2501–2520 (GCTCCCTCACATCCGTATCC) (SEQ ID NO: 5) was defined as INT21 primer; and the primer for the complementary chain of the 20-nucleotide sequence at nucleotide numbers (positions) 3144–3161 (GCATAAATCAGCCGTTTGCG) (SEQ ID NO: 6) was defined as INT20.

2-2. Int Gene

Figure 3:
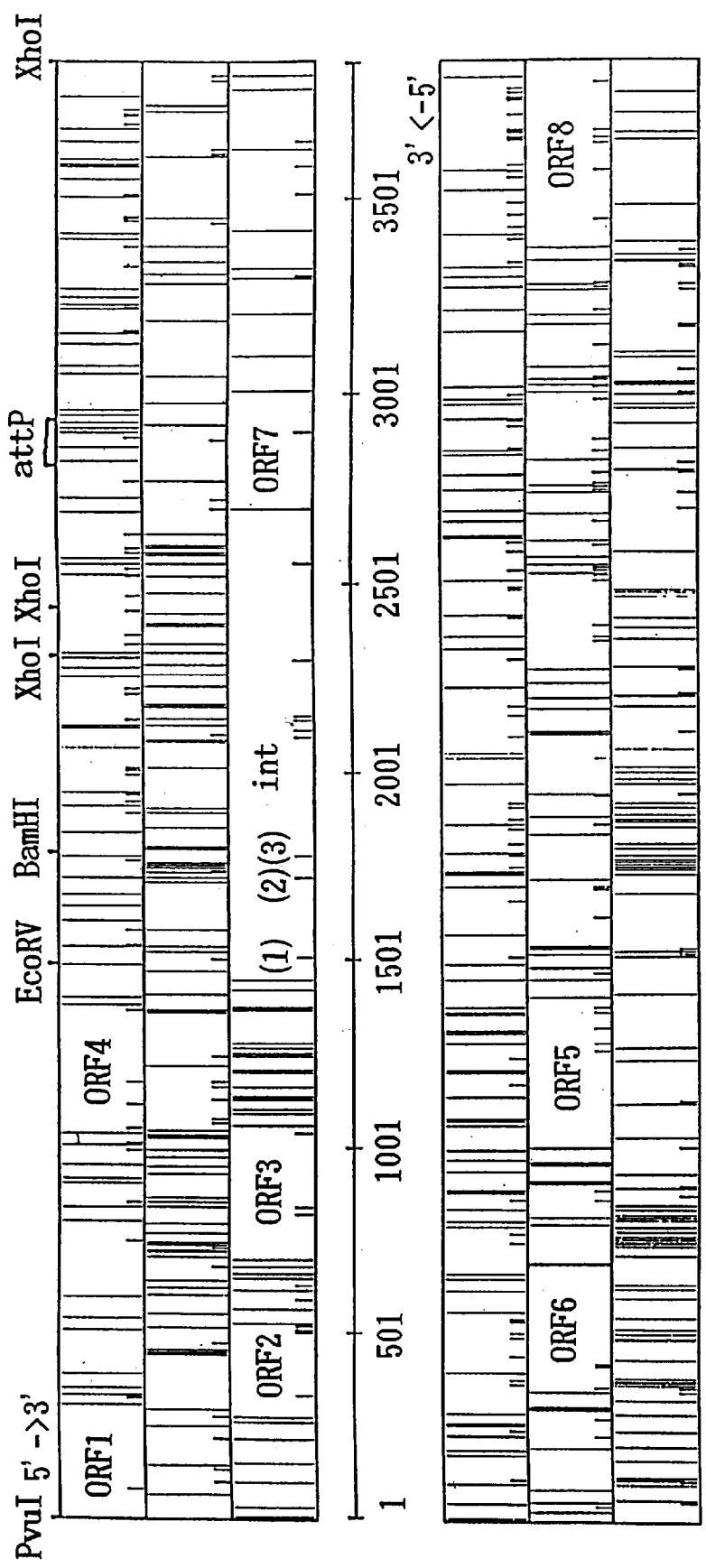
FIG. 3 is an explanatory view of the screening result of the ORF in SQ ID No.1.

ORFs were screened from a region with a determined DNA nucleotide sequence, together with the screening of a similar region between the translation products thereof and the amino acid sequences of known proteins. FIG. 3 is an explanatory view of the screening results of the ORF in the PvuI (1)—XhoI (3849) region including the Int and attP of SEQ ID No.1. In the figure, a long bar expresses a termination codon, while a short bar expresses an initiation codon (ATG or GTG). In the top three columns of the figure, the translation direction is shown from light to right. ORFs with 200 nucleotides or more are attached with names (ORF1 to 8, Int). Major restriction cleavage sites and the attP core region are also shown in the figure.

As shown in FIG. 3, a large ORF was found between nucleotide numbers 1509 to 2690. The translation product of the ORF (as shown in SEQ ID No.1) and the amino acid sequences of known proteins were subjected to screening of similar regions. Consequently, greater overall similarity was found between the translation product and the site-specific recombination enzyme (integrase) responsible for the prophage recombination of the phage L54a of *Staphylococcus aureus* (Reference G: Z. H. Ye & C. Y. Lee. Nucleotide sequence and genetic characterization of staphylococcal bacteriophage L54a "int" and "xis" gene. J. Bacteriol. 171: 4146–4153, 1989).

FIG. 4 is an explanatory view of the comparison in amino acid sequence between the putative integrase protein of φFSW (when the translation is initiated at the first Met (at nucleotide numbers (positions) 1509–1511) and the integrase protein of phage L54a of *Staphylococcus aureus*. In the figure, the symbol "*" represents the same amino acid; and the symbol "." represents an amino acid with similar properties. Additionally, the highly conserved regions, namely domain 1 and domain 2, are both enclosed with a square.

FIGS. 5a and 5b are explanatory views of the comparison in amino acid sequence between the two highly conserved regions (domain 1 and domain 2) found in the integrases of various phages and transposon. In the figures, four amino acids never replaceable with alternatives are attached with "*", while particularly highly conserved amino acids are underlined. Additionally, for φFSW, the same amino acid sequence as the consensus sequence is also underlined.

As shown in FIGS. 5a and 5b, two highly conserved regions called domain 1 and domain 2 are found in the site-specific recombination enzymes called integrases of various phages and transposon (Reference A: L. Dupont, B. Bizent-Bonhoure, M. Coddevile, F. Auvray & P. Ritzenthaler. Characterization of genetic elements required for site-specific integration of *Lactobacillus delbrueckii* subsp. *bulgaricus* bacteriophage mv4 and construction of an integration proficient vector for *Lactobacillus plantarum*. J. Bacteriol. 177: 586–595, 1995); and amino acid sequences corresponding to the regions are also found in the translation product of the ORF.

Supposing that the ORF coded for the integrase of φFSW, the ORF was defined as Int.

Based on the experiments concerning the presence or absence of the ribosomal RNA binding region immediately upstream the Int and on the experiments concerning the plasmid insertion described below, any one of the first, second and third Mets was suggested as the translation initiation point of the Int. The possible molecular weight of Int (product of the Int gene) was 45 k, given that the first Met was the translation initiation point; the possible molecular weight of Int (product of the Int gene) was 37 k, given that the second Met was the translation initiation point; and the possible molecular weight of Int (product of the Int gene) was 35 k, given that the third Met was the translation initiation point. Additionally, the estimated isoelectric point is 9.8 in any case, indicating that the Int is a basic protein capable of binding to DNA. Immediately downstream the translation region was present as inverse repetitious sequence capable of forming a stem-loop structure.

The translation product of ORF8 (the N-terminal nucleotide sequence not yet elucidated) was partially similar to proteins involved in cell wall lysis of Gram-positive bacteria, such as autolysins (N-acetylmuramoyl-L-alanine amidase, Accession Nos. P37710 and P39046) of bacteria of genus Enterococcus, and the proteins (P60, Accession Nos. Q01837, Q01839 and Q01838) responsible for the cellular infiltration of bacteria of genus Listeria.

FIG. 6 is an explanatory view of the homology in amino acid sequence between the protein possibly encoded by ORF8 and the autolysin (N-acetylmuramoyl-L-alanine amidase) derived from *Enterococcus faecalis*. In the figure, the symbol "*" represents the same amino acid; and the symbol "." represents an amino acid with similar properties. On the basis of the DNA sequence determined, a first amino acid was speculated as shown in the figure and defined as 1. As shown in the figure, it was confirmed that ORF8 was possibly the structural gene of the enzyme with the function to solubilize the cell wall of a host during the proliferation of φFSW.

As has been described above, an ORF capable of encoding a protein with the largest molecular weight of 45 k was found. By screening a region with similarity to the amino acid sequences of known proteins, overall or partial similarity was found between the ORF and the amino acid sequences of various phages and transposon. It was believed that the ORF encoded the integrase of concerning φFSW, so the ORF was defined as Int.

2-3. Isolation and Structure of Chromosomes of attR, attL and attB Regions

So as to demonstrate the recombination site (attP: present on the 1.3-kb XhoI DNA fragment) on the phage genome and the recombination site (attB) in the chromosome, then, a region containing the prophage integration site (attL and attR) in a φFSW-lysogenic bacterium was amplified by Tail-PCR, to elucidate the DNA sequence.

More specifically, it has been well known that the phage genome of φFSW when lysogenized is integrated at a specific site in the chromosome of a non-φFSW-lysogenic bacterium through Campbell-type site-specific recombination, which is to be prepared as a prophage. More specifically, cleavage and reunion should occur at a specific site (designated as attP) between the XhoI cleavage sites present at 13.8 kb and 15.1 kb on the phage restriction map and a specific site (designated as attB) in the chromosome.

Because the DNA sequence of the attP and therearound was determined, a portion corresponding to the attP in the lysogenic bacterium (YIT9018) was isolated by Tail-PCR, to examine the DNA sequence thereof. The results are shown in FIG. 7. FIG. 7 is an explanatory view of the comparison between the homologous region found in attP, attR, attL and attB and the DNA sequences around the region. By using primers prepared on the basis of the DNA sequences of attR and attL (INT25 "GATGGAAACCGTTGTCTGGG" (SEQ ID NO:7) and INT27 "TCGCGATGTCGTTTATCCCC" (SEQ ID NO:8), the presence of the attB region in the non-φFSW-lysogenic bacterial strain YIT9029 was confirmed. The DNA sequence of the thus confirmed attB is also shown in FIG. 7. Herein, no attR or attL was confirmed structurally in the YIT9029.

Subsequently, attP, attR, attL and attB were structurally compared, so that a homologous region of 40 nucleotides was found and defined as the core sequence (enclosed with a square). It is evident that site-specific recombination has occurred at the region. Characteristically, the core sequence is fairly longer than those in phages where recombination of other Campbell types occurs. Additionally, a palindrome structure including restriction enzyme recognition sites is also observed. In the figure, furthermore, the nucleotide sequences on the left sides of the core sequence are highly similar to each other.

As shown in SEQ ID No.1, the attP core sequence was present immediately downstream the inverse repetitious sequence around the Int gene (SEQ ID No. 1; nucleotide numbers (positions) 2587–2896). It was confirmed that this was common to the case of phages where other Campbell types of recombination occurred.

Alternatively, a DNA sequence including the attB region in YIT9029 as the non-φFSW-lysogenic bacterium is shown as SEQ ID No.3 in the Sequence Listing, while the amino acid sequence encoded by a part of SEQ ID No.3 is shown as SEQ ID No.4. Major restriction enzymes with relation to the nucleotide sequence of SEQ ID No.3 and the restriction cleavage sites thereof are as follows; PstI (nucleotide numbers (positions) 1–6), XmnI (nucleotide numbers (positions) 1190–1199), and Eco52I (nucleotide numbers (positions) 1208–1213). Furthermore, the attB core sequence is at nucleotide numbers (positions) 1183–1222. Still furthermore, the attB core sequence is positioned at nucleotide numbers (positions) 1183–1222. The same nucleotide sequence (20 nucleotides) as the sequence of INT25 primer is at nucleotide numbers (positions) 884–903; the nucleotide sequence (20 nucleotides) as the complementary sequence of the INT primer is at nucleotide numbers (positions) 1463–1482: and furthermore, the termination codon of the ORFattB described below is TAA-TAG at nucleotide numbers (positions) 1257–1262.

Figure 8:
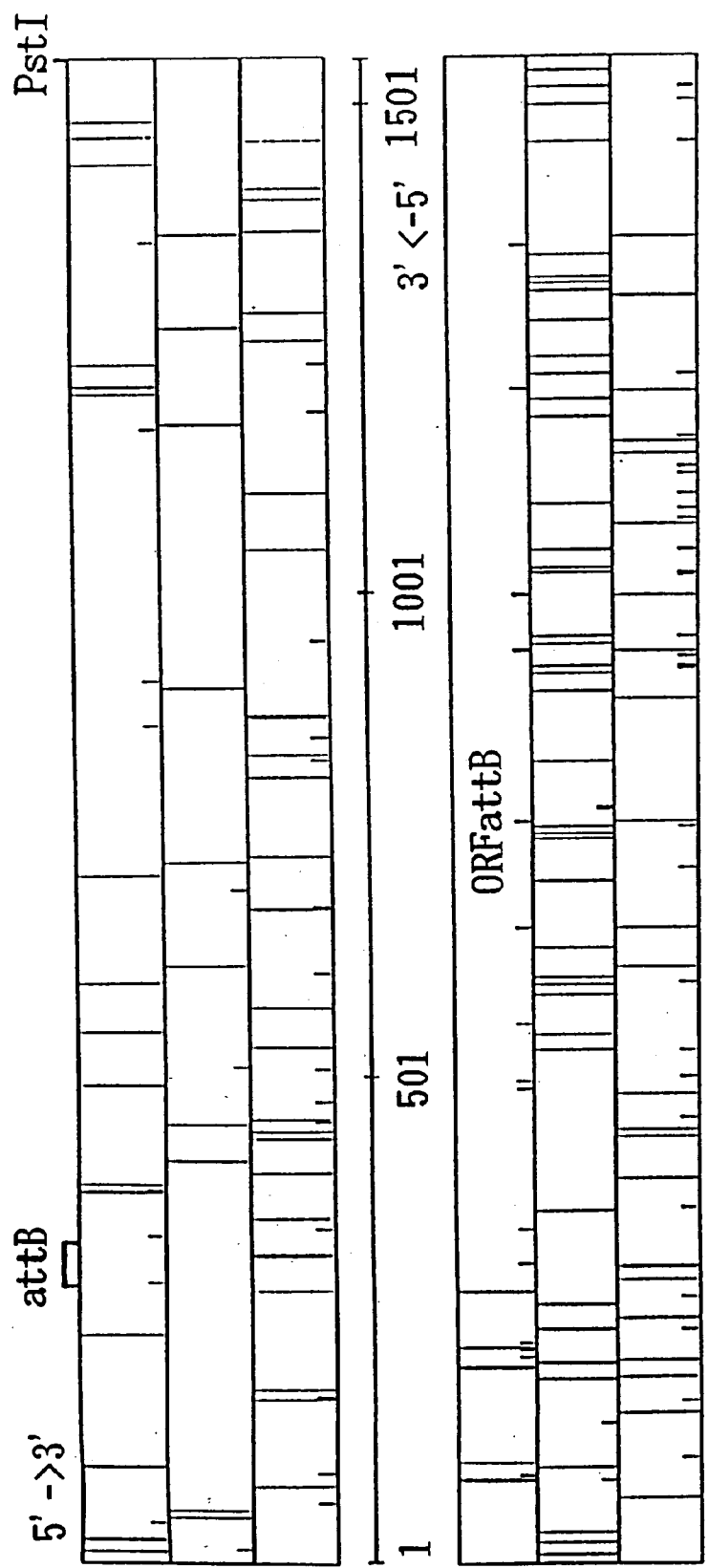
FIG. 8 is an explanatory view of the screening result of ORF in SEQ ID No.3.

Additionally, FIG. 8 is an explanatory view of the screening result of ORF in SEQ ID No.3. In the figure, a long bar expresses a termination codon and a short bar expresses an initiation codon (ATG or GTG) in each frame. The translation direction in the top three columns in the figure is from left to right. Still furthermore, a region having an amino acid sequence similar to the amino acid sequence of the translation product of the ORF expanding most of the region (designated as ORFattB; the N-terminal DNA sequence not yet determined) was screened out of the amino acid sequences of known proteins. FIG. 9a is an explanatory view of the comparison in amino acid sequence between the translation product of the ORF (ORFattB) in SEQ ID No.3 and the protein of glucose-6-phosphatase isomerase A derived from *Bacillus stearothermophilus*; and FIG. 9b is an explanatory view of the comparison in amino acid sequence between the translation product of the ORF (ORFattB) and the protein of glucose-6-phosphatase isomerase B.

A higher degree of overall similarity was observed between the translation product and glucose 6-phosphatase isomerases A and B (Accession Nos. P13375 and P13376, respectively) (FIGS. 9a and 9b). When prophage recombination occurred, only one amino acid Pro at the C terminus of the translation product was replaced with Leu, while the ORFattB was mostly conserved. Therefore, even if the ORFattB for glucose 6-phosphate isomerase for example is an essential gene for the growth of a host, the ORFattB possibly may not be inactivated even if φFSW is lysogenized.

2-4. Vector for *Lactobacillus Casei*

Plasmid pMSK742 was recovered by inserting a DNA fragment carrying the Int- and attP regions of φFSW into plasmid pMSK721 with an erythromycin (Em) resistant gene, never replicable in *L. casei* strain YIT9029 but expressible therein, and subsequently deleting the tetracycline resistant gene therefrom.

More specifically, plasmid pMSK721 (Reference E) carries a chemically resistant gene (erythromycin (Em) resistant gene derived from *Enterococcus faecalis*), never replicable in the strain YIT9029 but expressible therein. By transferring the DNA fragment carrying the Int- and attP regions derived from φFSW into the plasmid pMSK721, plasmid pMSK742 was recovered.

FIG. 1 is a restriction map of plasmid pMSK742. As shown in the figure, the plasmid carries an EcoRV(1506)-FspI(3759) region as a DNA fragment carrying the Int- and attP regions.

The resulting plasmid pMSK742 was transferred into a *L. casei* strain YIT 9029 by electroporation. The plasmid pMSK 742 generated a transformation recombinant with Em resistance at a frequency of about $10^3$/μg DNA, but once the Int region was deleted from the plasmid, no transformation recombinant with Em resistance could be recovered. It was apparently revealed that the int was essential so as to recover a transformation recombinant with Em resistance.

Consequently, a transformation recombinant with Em resistance was recovered at a frequency of about $10^3$/μg DNA in a plasmid harboring a PvuI (3)—FspI (3759) region and an EcoRV (1506)—FspI (3759) region. Alternatively, a transformation recombinant with Em resistance could not be recovered in a plasmid harboring a BamHI (1771)—FspI (3759) region interposing the Int region therein. Therefore, it was apparently shown that the Int was essential for recovering a transformation recombinant with Em resistance.

Hence, ORFs 1 to 6 are not necessary for recovering a transformation recombinant with Em resistance. Even when the Met described above in section 2-1 was used as a translation initiation point of the Int gene in pMSK742, a sequence ( . . . '5GGGGGATCCGTCGAATCATG3' . . . (SEQ ID NO:9)) functioning as a ribosome binding region could be recovered, after the sequence was cleaved with EcoRV and was then linked to a vector.

By PCR, Southern hybridization and DNA sequencing, the structures of attB, attR and attL in the transformation recombinant with Em resistance were analyzed. Consequently, the same attR and attL structures were found in all the analyzed transformation recombinants as in the case of the φFSW lysogenic phage, but no attB structure was confirmed (data not shown). Accordingly, it was shown that plasmids such as pMSK742 were integrated into the YIT9029 chromosome by the same mechanism as for the formation of prophage owing to the integration of the φFSW genome in the chromosome.

Because such chromosomal integration was found in a plasmid of a type where the tetracycline resistant gene from *Enterococcus faecalis* was linked to pMSK742 (data not shown), it was revealed that pMSK 742 could be used as a vector of a recombination type into the chromosome of YIT9029.

As has been described above, the foreign gene-inserted plasmid per se in the resulting vector was transferred into the chromosome of a host bacterium, and therefore, the stability of the vector is effectively stable. Advantageously, a recombination-type vector capable of the chromosome transfer in the *L. casei* strain YIT9029, in particular, can be recovered.

3. Summary of the Method for Transferring a Foreign Gene

A transformation recombinant was recovered by using a chromosome transfer-type vector pMSK742 where the site-specific recombination enzyme integrase for prophage transfer and integration is contained in the YIT9029 phage φFSW. The resulting transformation recombinant carries a plasmid DNA replication origin (derived from a different species) for the amplification of vector plasmids in *E. coli*, an Em resistant gene (derived from a different species), and an integrase gene (derived from the same species) in addition to the objective gene. It was supposed that these three regions were necessary for a series of procedures until transfer but the regions were not any more necessary for stably retaining the objective gene in the cells of YIT9029. Hence, the gene regions derived from a different vector species were purposely deleted.

A vector containing the attP region between a first partial sequence (A-B) lacking one terminal region of the objective foreign gene (A-B-C) to be transferred into the chromosome and a second partial sequence (B-C) lacking the other terminal region thereof was prepared, and by subsequently transferring the vector in the chromosome of a host *L. casei* bacterium, a plasmid was prepared for the purpose of deleting unnecessary gene regions through homologous recombination.

FIGS. 10a to 10d are schematic explanatory views depicting the processes of the method for transferring the foreign gene into the chromosome in one example in accordance with the present invention. The design and procedures are described in more detail with reference to FIGS. 10a to 10d.

Process a:

As shown in FIG. 10a, a second partial sequence (B-C) lacking the N-terminus of the objective gene and a first partial sequence (A-B) lacking the C- terminus thereof are arranged in the same direction on the two sides of the site-specific recombination site attP on the phage genome on the vector plasmid, and thereafter an Em resistant gene (Em) a plasmid DNA replication origin (ori) for *E. coli*, and the integrase gene (int) are arranged on the opposite side of the attP against the two defective genes.

Process b:

By transferring the plasmid DNA into the YIT9029 cell, a strain with the plasmid integrated on the YIT9029 chromosome (10) via site-specific recombination between the attP and attB by integrase was selected by using the Em resistance as a marker. As shown in FIG. 10b, supposedly, attL, the C-terminus-deleted objective gene (group) (A-B), the replication origin (ori) for plasmid DNA for E. coli, the Em resistant gene (Em), the integrase gene (int), the N-terminus-deleted objective gene (group) (B-C) and attR are arranged in this sequential order.

Process c:

Because the region B common to the two defective objective genes (groups) is homologous, a possibility is suggested that a part interposed between two regions Bs in some of the resulting transformation recombinants may be deleted by a homologous recombination mechanism essential to cells (FIG. 10c). In this case, attL, the complete objective gene (group) (A-B-C) and attR are aligned in this order in the DNA-transfected part of the deletion chromosome, so that it is suggested that the phenotype of the deletion recombinant is Em sensitive and ABC+ (FIG. 10d). More specifically, unnecessary genes derived from a different species and the like have been deleted on the resulting deletion recombinant.

4. Integration of Cm Resistant Gene

By using a Cm resistant gene (CAT) as a model gene (objective gene), an integration-type plasmid was actually prepared, in which some deletion might potentially occur.

As an objective gene to be integrated in the chromosome of YIT9029, the Cm resistant gene derived from plasmid pC194 of Staphylococcus aureus (S. aureus) was selected, taking account of the expression and selectivity in the strain and E. coli, restriction cleavage sites in the gene and the length of the gene. The structural gene encodes 216 amino acid residues, having a cleavage site with restriction endonuclease MunI at a position corresponding to the 9th amino acid residue from the N terminus and a cleavage site of restriction endonuclease VspI at a position corresponding to the 42nd amino acid residue from the C terminus.

Figure 11:
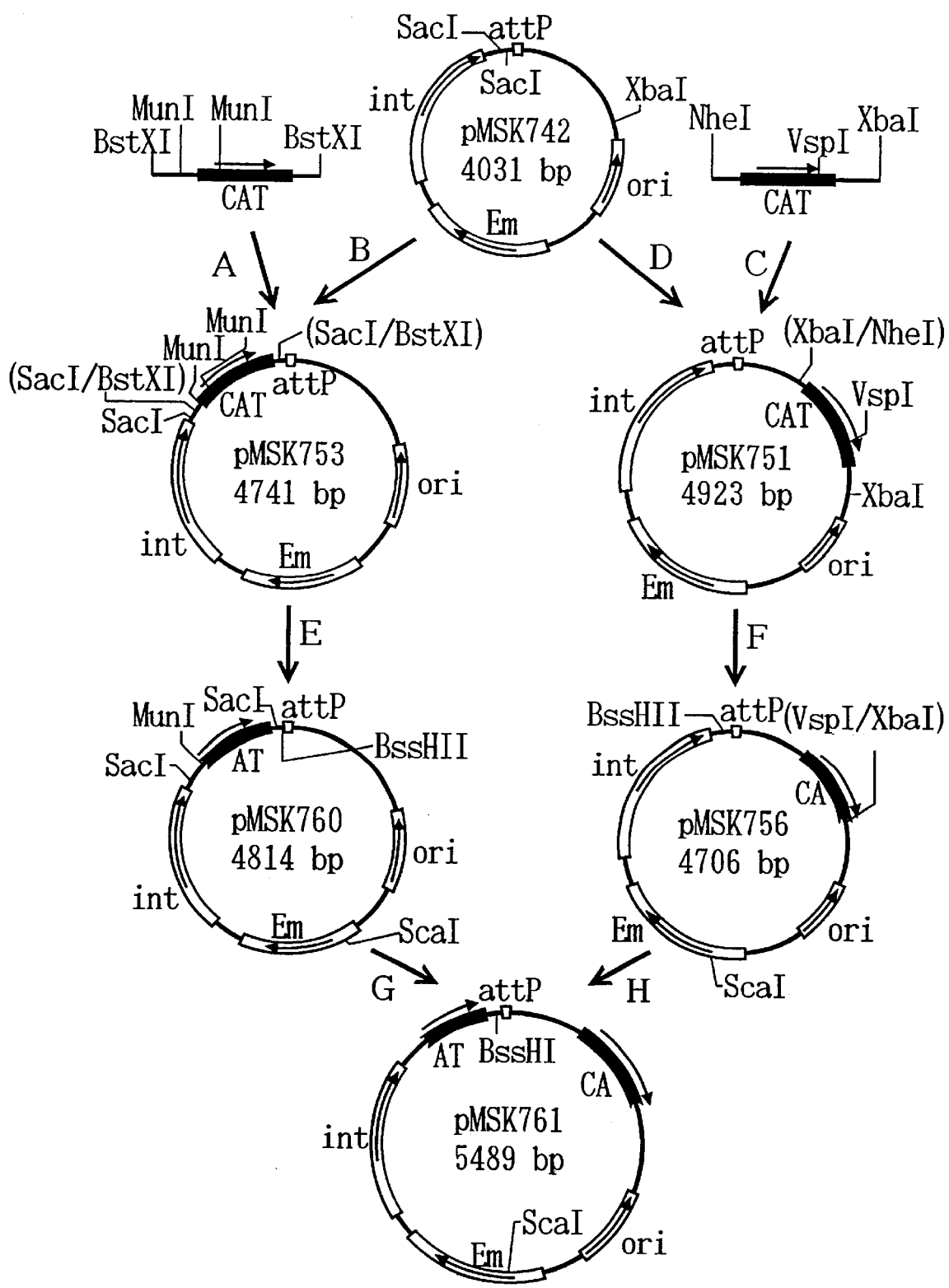
FIG. 11 is an explanatory view depicting the flow of the preparation of plasmid pMSK761 from pMSK742.

Following the chart in FIG. 11, an objective recombination-type plasmid was prepared. Two types of plasmids, namely pMSK755 and pMSK751, were first prepared, where the full-length Cm gene (CAT) was inserted into both the sides of attP.

More specifically, PMSK 753 was generated by the PCR amplification of a fragment (11a) carrying the Cm resistant gene of pC194 and including BstXI cleavage. sites at both the termini and a MunI cleavage site arranged just inside the BstXI cleavage site on the side of the N terminus of the structural gene, followed by the cleavage thereof with BstXI (process A) and subsequent conjugation of the resulting cleavage fragment to the SacI partial digestion fragment of pMSK742 dimer DNA (Process B). In a similar manner, pMSK751 was generated by the PCR amplification of a fragment (11b) carrying the Cm resistant gene of pC194 and containing an NheI cleavage site at the N terminus of the structural gene and an XbaI cleavage site arranged at the C terminus, the cleavage thereof with NheI and XbaI (process C), and subsequent conjugation of the resulting cleavage fragment with the XbaI complete digestion fragment of pMSK742 DNA (Process D). These two plasmids carry the Em resistant gene (Em), the plasmid DNA replication origin (ori) for E. coli, and the integrase gene (int) in addition to the Cm gene (CAT).

By using each of these plasmids, YIT9029 was transformed at a frequency of $10^3$/μg DNA or more, whereby it was confirmed that each plasmid was integrated through attP and attB into the chromosome of a transformation recombinant and that Em resistance was expressed concurrently with the expression of Cm resistance. More specifically, at 2.5 μg/mL Cm in a culture medium, a strain carrying the Cm resistant gene could grow therein but the parent strain could never grow therein.

Then, the Cm resistant genes in the individual plasmids pMSK753 and pMSK751 were deleted. More specifically, the MunI site of pMSK753 DNA was digested (Process E) to recover pMSK760, while pMSK751 DNA was digested with XbaI and VspI (Process F) to recover pMSK756. The recombinants from YIT9029 transformation with these plasmids were Cm sensitive at 2.5 μg/mL.

Figure 12:
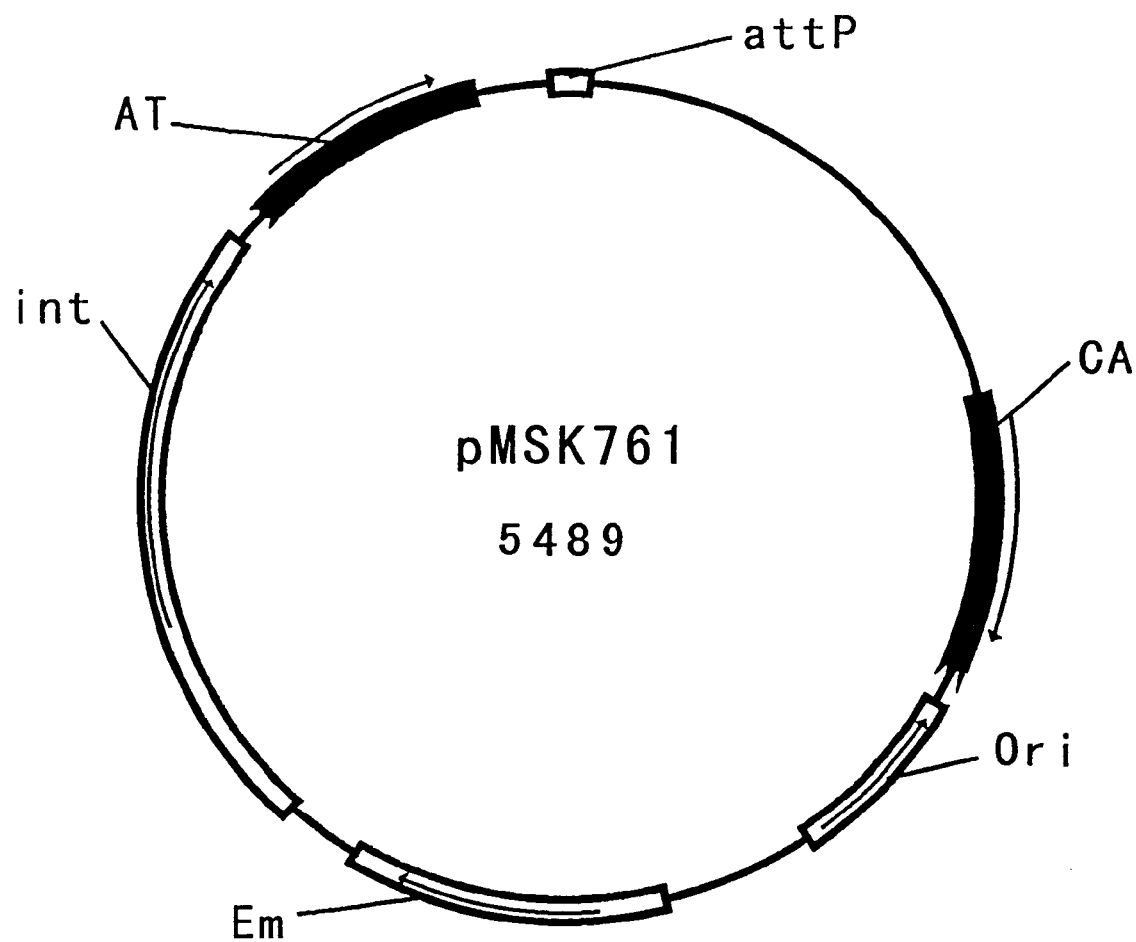
FIG. 12 is an explanatory view depicting the structure of the plasmid pMSK761 recovered as shown in FIG. 11.

Subsequently, both the DNAs of pMSK760 and pMSK756 were individually digested with BssHII and ScaI (Processes G and H), and by subsequently linking together the fragments each carrying the defective Cm gene, an objective plasmid pMSK761 was recovered. The structure of pMSK761 is shown in FIG. 12. The length of the homologous region common to the two defective genes was 494 nucleotides; and the distance between the two defective Cm genes not on the side en route of attP was 3545 nucleotides.

5. Procurement of Transformation Recombinant and Screening of Cm Expressing Strain pMSK761 recovered above in section 4 was integrated into the chromosome of YIT9029 while unnecessary genes were deleted. YIT9029 was transformed by using pMSK761, to recover an Em resistant transformation recombinant at the same frequency as that for pMSK755, and all of the resulting recombinants were sensitive to Cm at 2.5 μg/mL.

The Em resistant, Cm sensitive strain was cultured in an MRS culture medium supplemented with 0.5 μg/mL Cm (non-selective and inducible concentration), for division over about 40 generations, and the resulting bacteria were then subjected to screening in a culture medium containing 2.5 μg/mL Cm, to separate Cm resistant strains at a frequency of $10^{-3}$. All the 16 Cm resistant strains were Em sensitive.

Alternatively, 2.5 μg/mL Cm resistant strains were separated at a frequency of $10^{-5}$ from pMSK756 and pMSK760 each having only one defective Cm gene. All the 16 strains assayed remained Em resistant. The frequency of $10^{-5}$ is not different from the separation frequency of a mutant strain with spontaneous resistance against 2.5 μg/mL Cm.

These results indicate that spontaneous homologous recombination inside cells occurred in the homologous region between the two defective Cm resistant genes in some of the transformation recombinants with the chromosome into which the DNA of pMSK761 was integrated, to generate the full-length Cm gene to exert the resistance, and that a region containing the Em resistant gene was deleted.

This is supported by the identified structure of the chromosome of the Em sensitive, Cm resistant strain by analysis on the basis of the DNA sequence of the PCR product. More specifically, the following two types of evidence could be demonstrated;

i) attL, the full-length Cm resistant gene and attR were aligned in this order and ii) not any of the replication origin for plasmid DNA for E. coli, the Em resistant gene or the integrase gene was present.

6. Stability of Transformation Recombinant of Chromosome Integration Type

Figure 13:
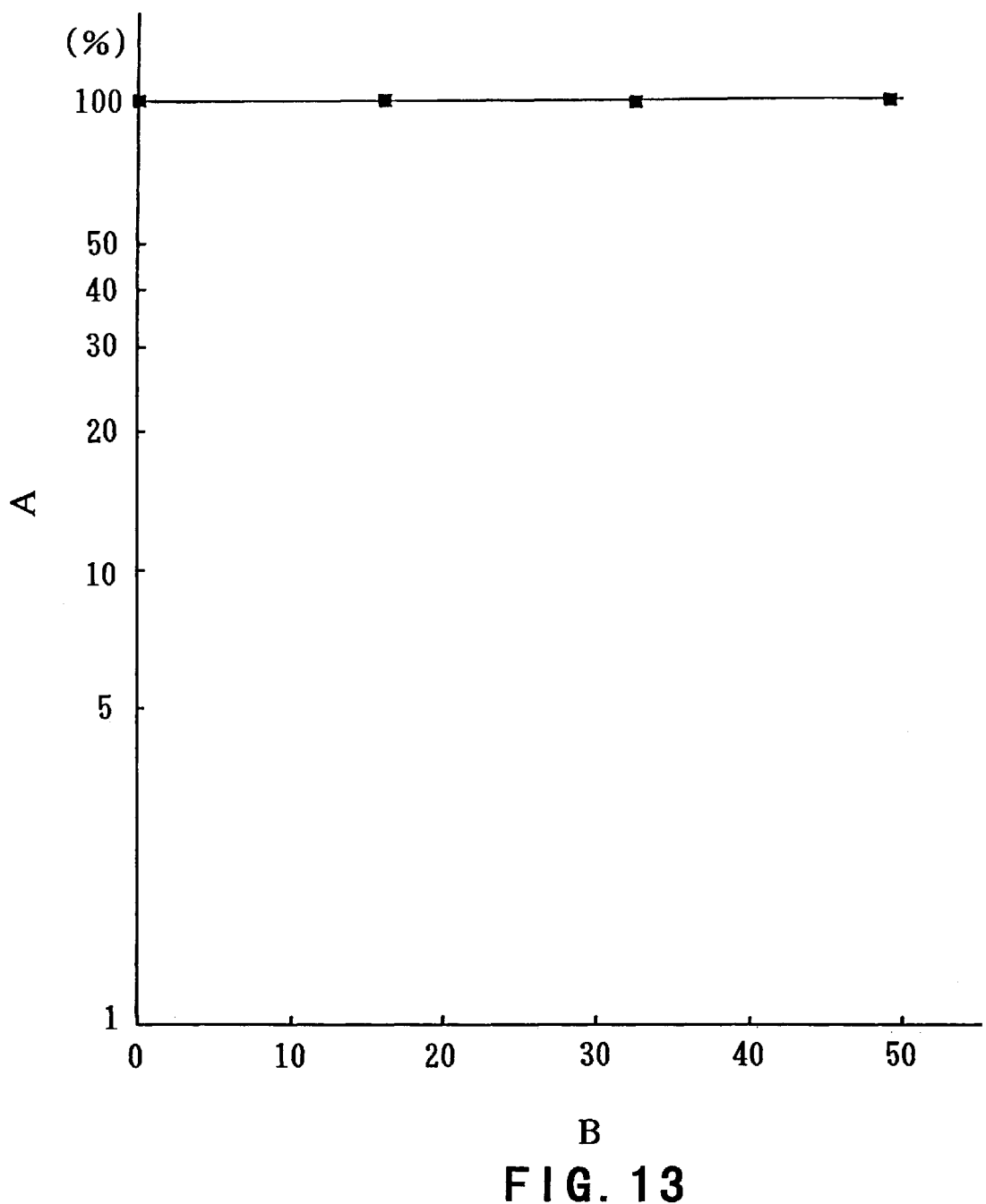
FIG. 13 depicts a graph of the stability test result of the chromosome-transferred recombinant recovered by transforming pMSK761, wherein the ratio of the chemically resistant strain is represented on the axis of ordinate (A) and the generation number is represented on the axis of abscissa (B).

The phenotypic stability of two Em sensitive, Cm resistant deletion strains recovered from pMSK761-trans formed recombinants as well as the ratio of chemically resistant strains after subculturing in a non-selective culture medium was determined, by counting the number of formed colonies on a selective plate and on a non-selective plate. As shown in FIG. 13, consequently, the chemically resistant character transferred in any of the YIT9029-transformed recombinants was conserved at a ratio of 100% over about 50 generations. About 5% of transformed strains transferred with a plasmid with the characteristic properties of the lysogenic phage exerted chemical resistance after division over about 50 generations.

Furthermore, groups each of 100 colonies derived from a cell after division over about 50 generations of an Em sensitive, Cm resistant, deletion strain derived from pMSK761-transformed recombinant were individually liquid cultured, to examine the chemical resistance. consequently, all the groups of the colonies retained the chemical resistance. Based on the aforementioned results, apparently, the integration of φFSW in the chromosome with integrase is very effective for stably retaining the objective gene. During the term, the presence or absence of the integrase gene did not have any influence on the stability.

As has been described above, in a vector of such chromosome integration type as prepared by utilizing the integrase of the phage φFSW of YIT9029, the objective gene for transfer into the chromosome was structurally modified to insert the gene in the vector. Consequently, via spontaneous homologous recombination after chromosomal integration, the Em resistant gene and plasmid DNA replication origin for *E. coli*, both derived from a different species, as well as the integrase gene derived from the same species, could be deleted from the finally grown strain.

The stability of the phenotype was also examined. The character transferred via the site-specific recombination between attP and attB by the integrase of φFSW was absolutely stable in the YIT9029-transformed recombinant under non-selective conditions even after cellular division for at least about 50 generations. During the term, no difference was found in stability between the presence and absence of the integrase gene.

As has been described above, the chromosomal integration by utilizing the integrase of φFSW as described above and the post-removal of unnecessary genes permit the growth of a recombinant in the strain YIT9029 in a stable fashion at high safety in a genetic engineering manner, together with the growth of the final strain as a non-recombinant type, depending on the type of the objective gene.

As has been described above, in accordance with the present invention, a method for transferring a foreign gene into a chromosome can be provided, advantageously, characterized in that unnecessary genes derived from vectors and the like, except for the foreign gene, can be deleted.

What is claimed is:

1. A method for integrating a foreign gene into a bacterial host chromosome comprising:
   (a) preparing a vector having properties of a lysogenic phase in which a lysogenic phage integration site is arranged between a first partial sequence and a second partial sequence of the foreign gene to be transferred, the first partial sequence lacking one terminal region of the sequence of said foreign gene, the second partial sequence lacking the other terminal region of the sequence of said foreign gene and having an overlapping region with a portion of the first partial sequence;
   (b) integrating the vector obtained in step (a) into the host chromosome at an integration site specific for the lysogenic phage to obtain recombinants; and
   (c) screening from among the recombinants obtained in step (b) a recombinant from which unnecessary genes originating in the vector have been deleted owing to a homologous recombination mechanism functioning in the overlapping region between the first partial sequence and the second partial sequence.

2. The method of claim 1, wherein the integration site is an attP site.

3. The method of claim 1, wherein the overlapping region has a length of a range between a lower limit length at which the homologous recombination mechanism functioning frequently occurs and an upper limit length at which no foreign gene expression occurs in the first and second partial sequences.

4. The method of claim 3, wherein the overlapping region has a length between 200 and 1,000 nucleotides.

5. The method of claim 1, wherein step (a) comprises arranging said first partial sequence and said second partial sequence toward the same direction with each other to align the individual termini N and C of the foreign gene so as to interpose the integration site of the lysogenic phage between the termini.

6. The method of claim 1, wherein step (c) comprises preliminarily confirming the expression of the foreign gene and using the expression as a marker to select said recombinant from which unnecessary genes originating in the vector have been denied.

7. The method of claim 1, wherein the vector is a *L. casei* vector.

8. The method of claim 1, wherein the vector is vector pMSK74.

9. The method of claim 1, wherein the foreign gene is a chloramphenicol resistant gene.

10. The method of claim 9, wherein the vector is vector pMSK74 and the overlapping region has a length of 400 to 600 nucleotides.

11. A method for integrating a foreign gene comprising regions A, B and C, wherein the region A and the region C represent partial sequences of different termini of the foreign gene; and the region B represents an arbitrary intermediate sequence between the partial sequences, into the chromosome of *Lactobacillus casei* comprising:

(a) preparing a *Lactobacillus casei* vector carrying the gene region of a site-specific recombination enzyme and an integration site into a host chromosome, wherein both the gene region and the integration site are derived from the lysogenic phase φFSW of *Lactobacillus casei* strain YIT9018, a chemically resistant gene region functioning in lactic acid bacteria and *Escherichia coli*, a replication origin functioning in *Escherichia coli*, and a cloning site in which the integration site is arranged between a first partial sequence containing regions A and B, but lacking the region C of the foreign gene to be transferred and a second partial sequence containing the regions B and C, but lacking the region A of the foreign gene to form a vector;

(b) integrating the vector obtained in step (a) into the chromosome of *Lactobacillus casei* to recover a recombinant; and (c) screening from among the recombinants obtained in step (b) a transformation recombinant from which unnecessary genes carrying the site-specific recombination enzyme region, the chemically resistant gene region and the replication origin have been deleted owing to a homologous recombination mechanism.

12. The method of claim 11, wherein the integration site is an attP site.

13. The method of claim 12, wherein the overlapping region has a length between 400 and 600 nucleotides.

14. The method of claim 11, wherein the site-specific recombinant enzyme is integrase.

15. The method of claim 11, wherein the chemically resistant gene region functioning in lactic and bacteria and *Escherichia coli* comprises an *Enterococcus faecalis* derived erythromycin resistant gene.

16. A *Lactobacillus casei* vector which permits the integration of a foreign gene into the chromosome of *Lactobacillus casei*, carrying:

the gene region of a site-specific recombination enzyme region and an attP region, both the site-specific recombination enzyme region and the attP region being derived from the lysogenic phage φFSW of *Lactobacillus casei* strain YIT9018;

a chemically resistant region functioning in lactic acid bacteria and *Escherichia coli*;

a replication origin derived from *Escherichia coli*; and a cloning site.

17. The vector of claim 16, wherein the site-specific recombination enzyme is integrase.

18. A *Lactobacillus casei* vector pMSK742 carrying the sequences of the restriction enzyme recognition sites as depicted in FIG. 1.

19. A transformation recombinant recovered by transferring a vector pMSK742 according to claim 18 into *Lactobacillus casei*.

* * * * *

SEQUENCE LISTING

```
<160> NUMBER OF SEQ ID NOS: 9

<210> SEQ ID NO 1
<211> LENGTH: 3849
<212> TYPE: DNA
<213> ORGANISM: Temperate phage
<220> FEATURE:
<221> NAME/KEY: RBS
<222> LOCATION: (1493)...(1499)
<221> NAME/KEY: RBS
<222> LOCATION: (1704)...(1708)
<221> NAME/KEY: RBS
<222> LOCATION: (1764)...(1770)
<221> NAME/KEY: CDS
<222> LOCATION: (1509)...(2690)
<300> PUBLICATION INFORMATION:
<301> AUTHORS: Ye, Z.Z, Lee, C.Y
<302> TITLE: Nucleotide sequence and genetic characterization of
       staphlococcal bacteriophage L54a int and xis genes.
<303> JOURNAL: J. Bacteriol.
<304> VOLUME: 171
<306> PAGES: 4146-4153
<307> DATE: 1989

<400> SEQUENCE: 1
cgatcgctta aagagattct tttttacact gatcgcgaca ctactaccat tcacaacgtc      60
ctagagaagc ctgtggtggc tgtttactgt ttcaatgagc tacaccactc atcgttgcta     120
ttgcgtgcaa aggccgttgt attgaccgct gaggaggcct taccaagctt tacggaaagc     180
ctcaattctt ttcaaaaatc gttacagtat gatcgacccg tcatcatccg ttgcaaccca     240
ctaaccgtca agattagata caacaatgac atcgagttca gcaagctaaa cgaaatcaa     300 gctcagttct tggagatgca cttatgaatg gtccagatac attaagcgag gcacacttca     360
ttggcctcat cattgttctt ataggcgtct acttcgccct gtttggccac aggcagcatt     420
ggattcgttg gctcattgac cctgataagc ccggcagcaa cctctggtgg gcagccgttt     480
```

-continued

```
ttatcattat cggcgcgctc atgatgatgg ttagaaagat gcaataattc ggcaccataa    540
agggggctag ttttcagaca agaaatagc cttccgcaga aggtctggag gtgaattcta     600
ttgataaaag atcgttttaa tttaaatccg tgcaatttag taggatttaa aatttcgcaa    660
cctagacgca atccaaatga gactgtttat caacttgagc ctttgaaaat tttgttaatt    720
ttgaactcgc gtgtaatttc atcattgatg gagttatccc tacctttaac attttcgcta    780
cgatttacaa tattagatta gattatccta tatcacctat ggctaccgct cagtctatga    840
ttgaagttac tgatgggcac acttttgaac cacttcaggc aaactttcat ttcaatattc    900
cactaaacca tctaagaaac ggcgacccta ctaatcaatt tgttgggatt gaattagctt    960
ggtcaattta tacgcctgaa gatccgcgta tttatgactc actaaagaat ggtgttctgt   1020
tccgaactag aactgaggtg attgacagca atggttaagc aaaatgttat accaatcaat   1080
ggaactccaa ttgaaaatcc tgctgatccg tattcaatgc aaaaacatga tacacttaag   1140
ccaaatacaa ctggcggagg tgagccacca atggatggag caaaaaaata cgcgactaaa   1200
aaacagctta agcgaaaagt aaaacgtatc gattcacgtt ttgatgaact tgacaaaagc   1260
attgattcaa agatcactaa ggcaaagttg caagcggtta tttggcttat tggtaccaca   1320
attgctggag ttgctgctgt tggctggatc ttcagcctca taatgaatag cattaagtaa   1380
cagaacgcaa atctcttcta acaattaaaa atccaaaata agagccctcc ttggggcttt   1440
tattttaacg aaaaaacgaa catacgtttg aattacaaac tctaagagtt caaaaggagt   1500 gcgatatc atg gca tca att agc tca tat aaa cta aaa gat ggc aaa aag     1550
          Met Ala Ser Ile Ser Ser Tyr Lys Leu Lys Asp Gly Lys Lys
            1               5                  10 gcc tgg gaa ttc tat ata ttc gct ggt gtt gat ccg cag aca gga aaa      1598
Ala Trp Glu Phe Tyr Ile Phe Ala Gly Val Asp Pro Gln Thr Gly Lys
 15              20                  25                  30 gaa ata aag atc cat cgg cgc ggt ttt cca acc gaa aaa ata gcc cag      1646
Glu Ile Lys Ile His Arg Arg Gly Phe Pro Thr Glu Lys Ile Ala Gln
             35                  40                  45 caa gaa gcc act ttg gcc gag gcc gaa ata atc aaa ggc cac tct cac      1694
Gln Glu Ala Thr Leu Ala Glu Ala Glu Ile Ile Lys Gly His Ser His
         50                  55                  60 tac caa act gaa aga att tta atg gct gat tat ctt aat cag tgg atc      1742
Tyr Gln Thr Glu Arg Ile Leu Met Ala Asp Tyr Leu Asn Gln Trp Ile
 65                  70                  75 act aag ctt aag gtt aat gtc aaa gag gga tcc atg att atc tat cga      1790
Thr Lys Leu Lys Val Asn Val Lys Glu Gly Ser Met Ile Ile Tyr Arg
         80                  85                  90 tat aat ctt aag aaa tac atc atc cca aaa att ggc gat att cga cta      1838
Tyr Asn Leu Lys Lys Tyr Ile Ile Pro Lys Ile Gly Asp Ile Arg Leu
 95                 100                 105                 110 gcc aaa tac acg ctt aag gaa cat cag gag ttc atc agc agt cta ttc      1886
Ala Lys Tyr Thr Leu Lys Glu His Gln Glu Phe Ile Ser Ser Leu Phe
            115                 120                 125 aat gat ggc ttg tct ctt aac aca gta aag ctc atc aat gga acg ttg      1934
Asn Asp Gly Leu Ser leu Asn Thr Val Lys Leu Ile Asn Gly Thr Leu
        130                 135                 140 cac aat gca tta aaa aaa gcc gtt gca att ggt tac att acc aaa aac      1982
His Asn Ala Leu Lys Lys Ala Val Ala Ile Gly Tyr Ile Thr Lys Asn
        145                 150                 155 cct acc gtt ggt gtc gag ttc agt gcg tat gct aaa gac aat tcc aaa      2030
Pro Thr Val Gly Val Glu Phe Ser Ala Tyr Ala Lys Asp Asn Ser Lys
        160                 165                 170
```

```
aaa ctt cac ttt tgg aca aaa gat caa gtt gga tct ttt ata gaa gca    2078
Lys Leu His Phe Trp Thr Lys Asp Gln Val Gly Ser Phe Ile Glu Ala
175                 180                 185                 190 gct gaa gaa gat aaa gag ccc atg tgg cta tca ttc ttt gtg acg ctg    2126
Ala Glu Glu Asp Lys Glu Pro Met Trp Leu Ser Phe Phe Val Thr Leu
                195                 200                 205 att gac tgc ggg ctt cgt gtg ggt gaa gcc atg gct ctc cgc tgg tca    2174
Ile Asp cys Gly Leu Arg Val Gly Glu Ala Met Ala Leu Arg Trp Ser
            210                 215                 220 gac att gac ttc agt aaa aat acc tta tca gtc aat gca aca cga atc    2222
Asp Ile Asp Phe Ser Lys Asn Thr Leu Ser Val Asn Ala Thr Arg Ile
            225                 230                 235 tat cgt gct gaa act gga tca aac gct ggc aaa ata gcg ctt gat cgt    2270
Tyr Arg Ala Glu Thr Gly Ser Asn Ala Gly Lys Ile Ala Leu Asp Arg
    240                 245                 250 ccc aaa aca tta agc tct aag aga acc gaa tac atg acc gct cga gta    2318
Pro Lys Thr Leu Ser Ser Lys Arg Thr Glu Tyr Met Thr Ala Arg Val
255                 260                 265                 270 aat gat ctt ctt caa caa caa tat gag cgc cat ttc agt cac ggc aat    2366
Asn Asp Leu leu Gln Gln Gln Tyr Glu Arg His Phe Ser His Gly Asn
                275                 280                 285 gta caa ggc ttt cgg ttt tct act agc cac aat aac gat ttt gtc ttc    2414
Val Gln Gly Phe Arg Phe Ser Thr Ser His Asn Asn Asp Phe Val Phe
            290                 295                 300 acc tat tcg tct gat gca aag ttt gga caa ccg ctc cga tct cga gca    2462
Thr Tyr Ser Ser Asp Ala Lys Phe Gly Gln Pro Leu Arg Ser Arg Ala
            305                 310                 315 act acc ggt gct ttt aat cgc atc acc aat cgg gct ggg ctc cct cac    2510
Thr Thr Gly Ala Phe Asn Arg Ile Thr Asn Arg Ala Gly Leu Pro His
            320                 325                 330 atc cgt atc cat gat tta aga cac acg cat gcc gtt tta atg cgt gag    2558
Ile Arg Ile His Asp Leu Arg His Thr His Ala Val Leu Met Arg Glu
335                 340                 345                 350 gca gga tta agc ctt gat gac atc aaa gat gat ctt ggg cat aaa gac    2606
Ala Gly Leu Ser Leu Asp Asp Ile Lys Asp Asp Leu Gly His Lys Asp
                355                 360                 365 att tca acc act caa att tat gct gaa atc tct ccg gca aaa aag aaa    2654
Ile Ser Thr Thr Gln Ile Tyr Ala Glu Ile Ser Pro Ala Lys Lys Lys
            370                 375                 380 gaa aac cat caa caa ttc gaa aaa tac cta aat cag tgaacacaaa         2700
Glu Asn His Gln Gln Phe Glu Lys Tyr Leu Asn Gln
                385                 390 aagagctcca gaatttgtgt ataagtccga agtcttcacc aaaacttcac cacggacttt  2760
tacaacatga ttctggagct ctttatttgc cacatttcaa atcgcgcaag cccttgccat  2820
taaaggcgcg cgttcaattc cttggtcata tcctcataac ccggacggcc gagcaatgcg  2880
aacatgttct tcttgttgtg atttgcttga acactgattt catagggttt caaatcgcgg  2940
gtgtaaaagc aaaaatagct atatatcaat ttcttaggtt tcacaatttc ggattcactt  3000
caccataact tcaccacgaa ttacttatat ttatattatt gcataagcaa ataagccctc  3060
cacccgcgtt agcgagcaga ggactttttg ttacctgata tatcaatatt cttctccgtc  3120
ccagccacgt agaccaggag gaccgcaaac ggctgattta tgctccaagg ccattgtcac  3180
agactgaacg gaggcaacag catctataag ttcatcagtt gaatgcttgt ctgaagcgga  3240
atccagcaac tctgaaacgg ctctcattaa gtcacgtctc acataacttt gctcaataac  3300
tcgtgcttga ccaattttt tagacatatg cactcaccct atttaaattt tttggtttca  3360
acggcaaccc attacttgat gtacaggctt tcacctgggt aaatcaaact gtagattgac  3420
```

```
ttgccattgt tggctgccag tgtgtacatg ctgatgccat acttgctggc aatactccag    3480
aagctgtcac cagagcggac tgtataatac gtgtggctta ccagcgaagt atatccagac    3540
gaacgcgagc catagctctc cccaccattc acgcccaagg caacataatg ataccgaccg    3600
gagtagctga ggtaccgtgc ccagacgtat gaaccgcgaa tatacacatg atcatacaca    3660
aggctctcac ccggcacata gctgccaact gccgtgtatc ctgtaccagc accagtgcgg    3720
atgttaacag tcgtggaagg cttgaaaaca ccagtttgcg catagtcgga atcactggct    3780
gcatttgatt tcgctggttg gcttggcacc ggtgttacag gtgctgacgg ggtttctggt    3840
tggctcgag                                                           3849
```

<210> SEQ ID NO 2
<211> LENGTH: 394
<212> TYPE: PRT
<213> ORGANISM: Temperate phage

<400> SEQUENCE: 2

```
Met Ala Ser Ile Ser Ser Tyr Lys Leu Lys Asp Gly Lys Lys Ala Trp
  1               5                  10                  15

Glu Phe Tyr Ile Phe Ala Gly Val Asp Pro Gln Thr Gly Lys Glu Ile
                 20                  25                  30

Lys Ile His Arg Arg Gly Phe Pro Thr Glu Lys Ile Ala Gln Gln Glu
             35                  40                  45

Ala Thr Leu Ala Glu Ala Glu Ile Ile Lys Gly His Ser His Tyr Gln
         50                  55                  60

Thr Glu Arg Ile Leu Met Ala Asp Tyr Leu Asn Gln Trp Ile Thr Lys
 65                  70                  75                  80

Leu Lys Val Asn Val Lys Glu Gly Ser Met Ile Ile Tyr Arg Tyr Asn
                     85                  90                  95

Leu Lys Lys Tyr Ile Ile Pro Lys Ile Gly Asp Ile Arg Leu Ala Lys
                100                 105                 110

Tyr Thr Leu Lys Glu His Gln Glu Phe Ile Ser Ser Leu Phe Asn Asp
            115                 120                 125

Gly Leu Ser Leu Asn Thr Val Lys Leu Ile Asn Gly Thr Leu His Asn
        130                 135                 140

Ala Leu Lys Lys Ala Val Ala Ile Gly Tyr Ile Thr Lys Asn Pro Thr
145                 150                 155                 160

Val Gly Val Glu Phe Ser Ala Tyr Ala Lys Asp Asn Ser Lys Lys Leu
                165                 170                 175

His Phe Trp Thr Lys Asp Gln Val Gly Ser Phe Ile Glu Ala Ala Glu
            180                 185                 190

Glu Asp Lys Glu Pro Met Trp Leu Ser Phe Phe Val Thr Leu Ile Asp
        195                 200                 205 cys Gly Leu Arg Val Gly Glu Ala Met Ala Leu Arg Trp Ser Asp Ile
    210                 215                 220

Asp Phe Ser Lys Asn Thr Leu Ser Val Asn Ala Thr Arg Ile Tyr Arg
225                 230                 235                 240

Ala Glu Thr Gly Ser Asn Ala Gly Lys Ile Ala Leu Asp Arg Pro Lys
                245                 250                 255

Thr Leu Ser Ser Lys Arg Thr Glu Tyr Met Thr Ala Arg Val Asn Asp
            260                 265                 270

Leu Leu Gln Gln Gln Tyr Glu Arg His Phe Ser His Gly Asn Val Gln
        275                 280                 285
```

```
Gly Phe Arg Phe Ser Thr Ser His Asn Asn Asp Phe Val Phe Thr Tyr
    290                 295                 300
Ser Ser Asp Ala Lys Phe Gly Gln Pro Leu Arg Ser Arg Ala Thr Thr
305                 310                 315                 320
Gly Ala Phe Asn Arg Ile Thr Asn Arg Ala Gly Leu Pro His Ile Arg
                325                 330                 335
Ile His Asp Leu Arg His Thr His Ala Val Leu Met Arg Glu Ala Gly
            340                 345                 350
Leu Ser Leu Asp Asp Ile Lys Asp Leu Gly His Lys Asp Ile Ser
        355                 360                 365
Thr Thr Gln Ile Tyr Ala Glu Ile Ser Pro Ala Lys Lys Glu Asn
    370                 375                 380
His Gln Gln Phe Glu Lys Tyr Leu Asn Gln
385                 390

<210> SEQ ID NO 3
<211> LENGTH: 1542
<212> TYPE: DNA
<213> ORGANISM: Lactobacillus casei

<400> SEQUENCE: 3 ct  gca gct gac aag gaa ttg cgt gaa gga aca ggt gct ggt aag gat      47
    Ala Ala Asp Lys Glu Leu Arg Glu Gly Thr Gly Ala Gly Lys Asp
    1               5                   10                  15 ttc cgc ggc ttt atc gat ttg cca gtc aac tat gac aag gac gaa ttt     95
Phe Arg Gly Phe Ile Asp Leu Pro Val Asn Tyr Asp Lys Asp Glu Phe
                20                  25                  30 gcc cgg atc aag gca gca gcc aag aaa gtt caa ggc aat tct caa gtc    143
Ala Arg Ile Lys Ala Ala Ala Lys Lys Val Gln Gly Asn Ser Gln Val
            35                  40                  45 ttt gtt gcg att ggg att ggc ggt tct tat tta ggc gca cgg atg gcg    191
Phe Val Ala Ile Gly Ile Gly Gly Ser Tyr Leu Gly Ala Arg Met Ala
        50                  55                  60 gtt gat ttt ctt tcc cag act ttc cgt aac ctt gac cct gat ctg aag    239
Val Asp Phe Leu Ser Gln Thr Phe Arg Asn Leu Asp Pro Asp Leu Lys
    65                  70                  75 ttc cca gaa gtt tat ttt gct ggt aac tca atc tct ggt act tat ctg    287
Phe Pro Glu Val Tyr Phe Ala Gly Asn Ser Ile Ser Gly Thr Tyr Leu
80                  85                  90                  95 gcg gac ttg ctt gac att att ggc gac cgt gac ttc tcg atc aac gtg    335
Ala Asp Leu Leu Asp Ile Ile Gly Asp Arg Asp Phe Ser Ile Asn Val
                100                 105                 110 atc agt aag tct ggt acc acg act gaa cct tca att gca ttc cgt gtt    383
Ile Ser Lys Ser Gly Thr Thr Thr Glu Pro Ser Ile Ala Phe Arg Val
            115                 120                 125 ctg aag gca aag ttg atc gaa aag tat ggc aaa gat ggc gca aag gaa    431
Leu Lys Ala Lys Leu Ile Glu Lys Tyr Gly Lys Asp Gly Ala Lys Glu
        130                 135                 140 cgg att tat gcg aca act gat cgt gcc aag ggt gcc ttg aaa caa gaa    479
Arg Ile Tyr Ala Thr Thr Asp Arg Ala Lys Gly Ala Leu Lys Gln Glu
    145                 150                 155 gca gac gca gaa ggc tat gaa gaa ttc gtt gtt cct gat gat gtc ggc    527
Ala Asp Ala Glu Gly Tyr Glu Glu Phe Val Val Pro Asp Asp Val Gly
160                 165                 170                 175 ggt cgg ttc tct gtg atg tcc gct gtt ggt ctg ttg cca atc gct gtt    575
Gly Arg Phe Ser Val Met Ser Ala Val Gly Leu Leu Pro Ile Ala Val
                180                 185                 190
```

```
gca ggc ggt gac att gac gaa atg atg cgt ggt ctc ggt gat ggt cgt    623
Ala Gly Gly Asp Ile Asp Glu Met Met Arg Gly Leu Gly Asp Gly Arg
        195                 200                 205 aag gca tac gct tca gct gat ttg aag gaa aac gaa gct tat cag tac    671
Lys Ala Tyr Ala Ser Ala Asp Leu Lys Glu Asn Glu Ala Tyr Gln Tyr
        210                 215                 220 gcc gca ttg cgg aac att ttg tat cgc aag ggc tat acc act gaa ttg    719
Ala Ala Leu Arg Asn Ile Leu Tyr Arg Lys Gly Tyr Thr Thr Glu Leu
    225                 230                 235 ttg gaa aac tac gaa cca acg ttg caa tac ctt ggc gaa tgg tgg aag    767
Leu Glu Asn Tyr Glu Pro Thr Leu Gln Tyr Leu Gly Glu Trp Trp Lys
240                 245                 250                 255 caa ttg atg ggt gaa tct gaa ggt aag gac cag aag ggg atc tat cct    815
Gln Leu Met Gly Glu Ser Glu Gly Lys Asp Gln Lys Gly Ile Tyr Pro
                260                 265                 270 tca agt gcc aac ttc agt act gac ctg cac agt ctt ggc caa tac att    863
Ser Ser Ala Asn Phe Ser Thr Asp Leu His Ser Leu Gly Gln Tyr Ile
            275                 280                 285 cag gaa ggt ctg cgc aac ctg atg gaa acc gtt gtc tgg gtt gaa gaa    911
Gln Glu Gly Leu Arg Asn Leu Met Glu Thr Val Val Trp Val Glu Glu
        290                 295                 300 cca aac cgc gac cta acc att cct gaa gat gct aac aac ctt gac ggc    959
Pro Asn Arg Asp Leu Thr Ile Pro Glu Asp Ala Asn Asn Leu Asp Gly
305                 310                 315 ctt ggc tac ttg gct ggc aag aag atg tcc ttc gtt aac cgc aag gcc    1007
Leu Gly Tyr Leu Ala Gly Lys Lys Met Ser Phe Val Asn Arg Lys Ala
320                 325                 330                 335 tat gaa ggg gtt gtt ctc gcc cac acc gat ggc ggc gtg cca gtt atg    1055
Tyr Glu Gly Val Val Leu Ala His Thr Asp Gly Gly Val Pro Val Met
                340                 345                 350 acc gtc tcc att cca aag cag gat gcc tac acc tta ggc tat ctg atc    1103
Thr Val Ser Ile Pro Lys Gln Asp Ala Tyr Thr Leu Gly Tyr Leu Ile
            355                 360                 365 tat ttc ttc gaa gct gtc gtt tca atc tcc ggc tac ctg aac ggg atc    1151
Tyr Phe Phe Glu Ala Val Val Ser Ile Ser Gly Tyr Leu Asn Gly Ile
        370                 375                 380 aac cca ttc aac cag cca ggt gtt gaa gcc tac aag aag aac atg ttc    1199
Asn Pro Phe Asn Gln Pro Gly Val Glu Ala Tyr Lys Lys Asn Met Phe
385                 390                 395 gca ttg ctc ggc cgt ccg ggt tac gag gat atg acc aag gaa ttg aac    1247
Ala Leu Leu Gly Arg Pro Gly Tyr Glu Asp Met Thr Lys Glu Leu Asn
400                 405                 410                 415 gca cgg cct                                                         1256
Ala Arg Pro taatagcgtg ggtttgaggt cgtttggata ggaaaaaatg agagcctcaa aattgtgttg    1316
taaatgttcg tgactgactt ttgactgaat agccaaaagg gtcaaaacat ttatgtacca    1376
attttgaggc tcttttttgtg tccgctggat tgccagtact ggctttcttt tggtgtatag    1436
actaaaaaca cggtgtgatt tcagcggggg ataaacgaca tcgcgaaatc aagcctatat    1496
ccatatattg acccaatatc taattggcat attaatatcg gcgttt                   1542

<210> SEQ ID NO 4
<211> LENGTH: 418
<212> TYPE: PRT
<213> ORGANISM: Lactobacillus casei

<400> SEQUENCE: 4

Ala Ala Asp Lys Glu Leu Arg Glu Gly Thr Gly Ala Gly Lys Asp Phe
 1               5                  10                  15
```

-continued

```
Arg Gly Phe Ile Asp Leu Pro Val Asn Tyr Asp Lys Asp Glu Phe Ala
             20                  25                  30

Arg Ile Lys Ala Ala Ala Lys Lys Val Gln Gly Asn Ser Gln Val Phe
         35                  40                  45

Val Ala Ile Gly Ile Gly Gly Ser Tyr Leu Gly Ala Arg Met Ala Val
     50                  55                  60

Asp Phe Leu Ser Gln Thr Phe Arg Asn Leu Asp Pro Asp Leu Lys Phe
 65                  70                  75                  80

Pro Glu Val Tyr Phe Ala Gly Asn Ser Ile Ser Gly Thr Tyr Leu Ala
                 85                  90                  95

Asp Leu Leu Asp Ile Ile Gly Asp Arg Asp Phe Ser Ile Asn Val Ile
             100                 105                 110

Ser Lys Ser Gly Thr Thr Thr Glu Pro Ser Ile Ala Phe Arg Val Leu
         115                 120                 125

Lys Ala Lys Leu Ile Glu Lys Tyr Gly Lys Asp Gly Ala Lys Glu Arg
 130                 135                 140

Ile Tyr Ala Thr Thr Asp Arg Ala Lys Gly Ala Leu Lys Gln Glu Ala
145                 150                 155                 160

Asp Ala Glu Gly Tyr Glu Glu Phe Val Val Pro Asp Asp Val Gly Gly
                 165                 170                 175

Arg Phe Ser Val Met Ser Ala Val Gly Leu Leu Pro Ile Ala Val Ala
             180                 185                 190

Gly Gly Asp Ile Asp Glu Met Met Arg Gly Leu Gly Asp Gly Arg Lys
         195                 200                 205

Ala Tyr Ala Ser Ala Asp Leu Lys Glu Asn Glu Ala Tyr Gln Tyr Ala
 210                 215                 220

Ala Leu Arg Asn Ile Leu Tyr Arg Lys Gly Tyr Thr Thr Glu Leu Leu
225                 230                 235                 240

Glu Asn Tyr Glu Pro Thr Leu Gln Tyr Leu Gly Glu Trp Trp Lys Gln
                 245                 250                 255

Leu Met Gly Glu Ser Glu Gly Lys Asp Gln Lys Gly Ile Tyr Pro Ser
             260                 265                 270

Ser Ala Asn Phe Ser Thr Asp Leu His Ser Leu Gly Gln Tyr Ile Gln
         275                 280                 285

Glu Gly Leu Arg Asn Leu Met Glu Thr Val Val Trp Val Glu Glu Pro
 290                 295                 300

Asn Arg Asp Leu Thr Ile Pro Glu Asp Ala Asn Asn Leu Asp Gly Leu
305                 310                 315                 320

Gly Tyr Leu Ala Gly Lys Lys Met Ser Phe Val Asn Arg Lys Ala Tyr
                 325                 330                 335

Glu Gly Val Val Leu Ala His Thr Asp Gly Gly Val Pro Val Met Thr
             340                 345                 350

Val Ser Ile Pro Lys Gln Asp Ala Tyr Thr Leu Gly Tyr Leu Ile Tyr
         355                 360                 365

Phe Phe Glu Ala Val Val Ser Ile Ser Gly Tyr Leu Asn Gly Ile Asn
 370                 375                 380

Pro Phe Asn Gln Pro Gly Val Glu Ala Tyr Lys Lys Asn Met Phe Ala
385                 390                 395                 400

Leu Leu Gly Arg Pro Gly Tyr Glu Asp Met Thr Lys Glu Leu Asn Ala
                 405                 410                 415

Arg Pro
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
gtcccctcac atccgtatcc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
gcataaatca gccgtttgcg                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gatggaaacc gttgtctggg                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tcgcgatgtc gtttatcccc                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: DNA
      Internal Fragment of Plasmid pMSK742.

<400> SEQUENCE: 9
gggggatccg tcgaatcatg                                                  20
```